(12) United States Patent
Mixson

(10) Patent No.: US 7,163,695 B2
(45) Date of Patent: *Jan. 16, 2007

(54) HISTIDINE COPOLYMER AND METHODS FOR USING SAME

(76) Inventor: A. James Mixson, 15620 Thistlebridge Dr., Rockville, MD (US) 20853

( * ) Notice: Subject to any disclaimer, the term of this patent is extended or adjusted under 35 U.S.C. 154(b) by 732 days.

This patent is subject to a terminal disclaimer.

(21) Appl. No.: 10/018,103

(22) PCT Filed: Dec. 20, 2000

(86) PCT No.: PCT/US00/34603

§ 371 (c)(1),
(2), (4) Date: Nov. 5, 2001

(87) PCT Pub. No.: WO01/47496

PCT Pub. Date: Jul. 5, 2001

(65) Prior Publication Data

US 2003/0045465 A1    Mar. 6, 2003

Related U.S. Application Data

(60) Provisional application No. 60/173,576, filed on Dec. 29, 1999.

(51) Int. Cl.
| | |
|---|---|
| A61K 9/14 | (2006.01) |
| A61K 38/16 | (2006.01) |
| A61K 48/00 | (2006.01) |
| C12N 15/88 | (2006.01) |
| C07K 4/00 | (2006.01) |
| C07K 7/00 | (2006.01) |
| C07K 14/00 | (2006.01) |

(52) U.S. Cl. .................. 424/486; 424/484; 435/320.1; 435/458; 530/300; 530/323; 530/324; 514/2; 514/44

(58) Field of Classification Search ...................... None
See application file for complete search history.

(56) References Cited

U.S. PATENT DOCUMENTS

| | | | |
|---|---|---|---|
| 4,847,240 A | | 7/1989 | Ryser et al. |
| 5,354,844 A | | 10/1994 | Beug et al. |
| 5,554,388 A | | 9/1996 | Illum |
| 5,670,347 A | * | 9/1997 | Gopal .................. 435/467 |
| 5,736,392 A | | 4/1998 | Hawley-Nelson et al. |
| 5,856,435 A | | 1/1999 | Bazile et al. |
| 5,985,354 A | | 11/1999 | Mathiowitz et al. |
| 6,051,429 A | * | 4/2000 | Hawley-Nelson et al. .. 435/458 |
| 6,113,946 A | * | 9/2000 | Szoka et al. ................. 424/486 |
| 6,312,727 B1 | * | 11/2001 | Schacht et al. ............. 424/490 |
| 6,372,499 B1 | * | 4/2002 | Midoux et al. ............. 435/455 |
| 6,475,004 B1 | * | 11/2002 | Shuey et al. ................. 439/157 |
| 2001/0006817 A1 | * | 7/2001 | Pack et al. ................... 435/440 |

FOREIGN PATENT DOCUMENTS

| | | |
|---|---|---|
| EP | 0 727 223 A1 | 4/1995 |
| WO | WO 98/22610 | 5/1998 |
| WO | WO 99/42091 | 8/1999 |
| WO | WO 00/32764 | 6/2000 |

OTHER PUBLICATIONS

Midoux et al., Membrane Permeabilization and Efficient Gene Transfer by a Peptide Containing Several Histindines. *Bioconjug Chem* 98, 9, 260-267, -1998-.
Midoux et al., Efficient Gene Transfer by Histidylated Polylysine/pDNA Complexes. *Bioconjugate Chem* 1999 May-Jun.; 10(3):4-6-411.
Chen et al., Co-polymer of histidine and lysine markedly enhances transfection efficiency of liposomes. *Gene Ther* Oct. 2000; 7(19):1698-1705.
Chen et al., Branched co-polymers of histidine and lysine are efficient carriers of plasmids. *Nucleic Acids Res* Mar. 15, 2001; 29(6);1334-1340.
Pichon et al., Histidylated oligolysines increase the transmembrane passage and the biological activity of antisense oligonucleotides. *Nucleic Acids Res* Jan. 15, 2000; 28(2):504-512.
Putnam et al., Polymer-based gene delivery with low cytotoxicity by a unique balance of side-chain termini. *Proc Natl Acad Sci USA* Jan. 30; 98(3):1200-1205.

* cited by examiner

*Primary Examiner*—Scott D. Priebe
(74) *Attorney, Agent, or Firm*—Connolly, Bove, Lodge & Hutz, LLP

(57) ABSTRACT

The invention provides a pharmaceutical agent delivery composition comprising: (i) a transport polymer comprising a linear or branched peptide having from about 10 to about 300 amino acid residues, having from about 5 to 100% histidine residues, and optionally having from 0 to about 95% non-histidine amino acid residues; (ii) at least one pharmaceutical agent; and optionally (iii) one or more intracellular delivery components in association with the transport polymer. The invention also provides methods for using such composition to deliver the pharmaceutical agent to the interior of cells.

51 Claims, 18 Drawing Sheets

HISTIDINE COPOLYMER AND METHODS FOR USING SAME

Figure 1:
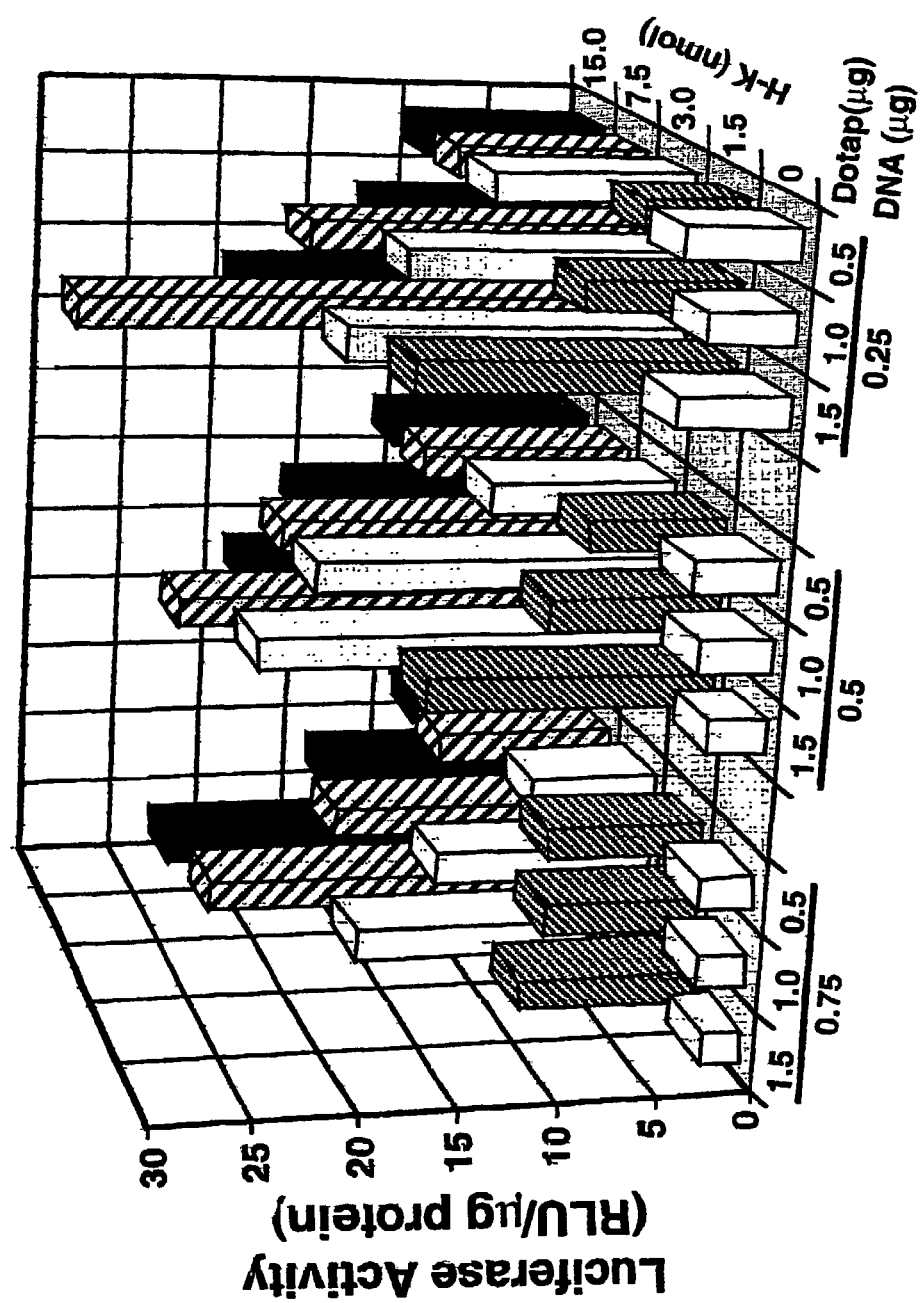

This application claims the benefit of U.S. Provisional Application No. 60/173,576, filed Dec. 29, 1999.

This work was supported by the National Institutes of Health (CA70394).

1. FIELD OF THE INVENTION

The present invention relates to transport polymers comprising histidine and to pharmaceutical agent delivery compositions comprising such transport polymers. The transport polymers and delivery compositions of the invention are useful in the delivery of pharmaceutical agents to the interior of a cell. Thus, the present invention relates further to methods of using the delivery compositions to deliver therapeutic, diagnostic, and/or cosmetic compounds to cells.

2. BACKGROUND AND PRIOR ART

Many scientific and commercial methods involve intracellular delivery of materials to the interior of cells. For example, in the medical field, treatment therapies can deliver pharmaceutical agents to the interior of cells. In the field of molecular biology, it is known to deliver genetic material and other biological compounds to the interior of a cell (i.e., transfection). One important application of intracellular delivery of nucleic acids is gene therapy. In addition to gene delivery, pharmaceutical agent delivery compositions can be used to deliver other therapeutic agents, as well as diagnostic and cosmetic agents.

With regard to gene therapy, recent advances in molecular biology have increased the scientific understanding of the genetic basis for disease. Modern tools have provided significant advances in gene therapy. It is now possible to produce nucleotide sequences capable of expressing therapeutic molecules and to package them in expression vectors. In the context of gene therapy, transfection systems are used to deliver the expression vectors to a subject's cells. Once delivered, the nucleic acid is expressed in the target cells to produce proteins and/or peptides. Although gene therapy is promising as a method of treating genetic based diseases, major obstacles remain. Progress in gene therapy has been limited by the lack of gene-delivery systems having a transfection efficiencies which are adequate to deliver therapeutically significant amounts of genetic materials and other pharmaceutical agents into target cells. Furthermore, nucleic acid delivery systems, in particular non-viral systems, have a significant reduction in transfection efficiency in the presence of serum. Success of gene therapy depends on the development of improved transfection systems, with higher transfection efficiency and increased resistance to serum.

Commonly used transfection systems can be grouped into viral and non-viral transfection systems.

2.1 Non-Viral Transfection Systems

Non-viral transfection systems have been explored as delivery mechanisms for genetic materials and other biological compounds. Such non-viral transfection systems include, for example, liposomal systems. A liposome is a compartment bounded by a lipid bilayer. Materials, such as DNA or protein, can be contained within a liposome, either in the liposome compartment, associated with the bilayer, or associated with the liposome exterior, and therapeutic materials can be delivered to the interior of a cell by endosomal uptake or by fusion of the agent-containing liposome with the cell membrane.

Cationic liposomes are the most commonly used non-viral delivery system for both in vitro (1–3) and in vivo (4–6) DNA transfection. A significant problem associated with cationic liposomes is their low transfection efficiency (7,8), both in vitro and in vivo. At least in vivo, this low transfection efficiency has been attributed to inactivation of liposomes by serum (9,10). On the other hand, cationic liposome carriers are relatively easy to produce in large quantities and exhibit minimal toxicity (11). Accordingly, significant effort is presently being devoted to improving the in vivo efficacy of liposomes.

Several recent developments have advanced the prospects for enhanced liposome transfection efficiency. In vivo transfection efficiency of liposomes has been enhanced by the development of new lipids (12) and by the replacement of DOPE (13) with cholesterol, as a helper lipid.

The addition of poly-L-lysine or protamine to cationic liposome carriers is known to enhance the transfection efficiency of liposomes (9,14–17). These highly basic polymers/proteins effectively condense the plasmid DNA, while liposomes neutralize the remainder of the negative charge of the DNA and provide a scaffold for the polymer:DNA complex. Although poly-L-lysine increases transfection of liposome carriers, the addition of serum during transfection markedly reduces the efficiency of this carrier. Thus, poly-L-lysine in combination with liposomes may be somewhat limited as a carrier in the presence of serum.

Lysosomotropic agents have also been used to increase transfection efficiency of liposomes and other cationic carriers. Lysosomotropic agents protect plasmids from hydrolytic digestion within endosomes and/or enable plasmids to escape from endosomes (18–25). These lysosomotropic agents include chloroquine, $NH_4CL$, monesisn, bafilomycin and brefeldin, which are weak amines that buffer the prelysosomal vesicles.

Other efforts at improving gene-delivery agents have focused on DNA-condensing and pH buffering properties (26–29). These efforts have yielded dendrimers (Superfect, polyethylenimine) and polyamidoamine whose single repeating subunit contains both a positive charge and buffering capacity. Such polymers have a single repeating subunit with two or more functional features, resulting in an inherent inflexibility, since binding and buffering properties within these polymers are fixed and cannot be varied. It is also likely that the currently available polymers will not be metabolizable, and with prolonged administration, these polymers are likely to be toxic. Previously, polymers with both DNA binding and buffering capacity (e.g. polyamidoamine) in combination with liposomes were found not to enhance transfection efficiency (15). In addition, a large molecular weight histidylated poly-L-lysine polymer has been recently reported in 3 of 4 cell lines to be significantly less effective (between 6 to 21 fold) than polyethylenimine (PEI), a commonly used carrier and one of the more effective carriers in gene transfer systems (30).

There is a need in the art for pharmaceutical agent delivery systems having transfection efficiencies sufficient to deliver therapeutically effective amounts of nucleic acid into cell. There is also a need in the art for carriers that are stable in serum in order for delivery systems to be effective both in vitro and in vito. Moreover, there is a continuing need in the art for improved non-viral pharmaceutical agent delivery systems capable of delivering pharmaceutical agents into the interior of cells in amounts sufficient to treat conditions such as metabolic and neoplastic conditions in humans.

2.2 Viral Transfection Systems

Various viral transfection systems are also known in the art, such as retroviruses (e.g., murine leukemia virus, avian, lentivirus), adenoviruses and adeno-associated viruses, herpes simplex viruses, rhinovirus, Sendai virus, and Poxviruses. These systems have been proposed for gene therapy. Combinations of viral vectors with non-viral delivery systems have also been utilized to enhance gene delivery (37–44). A significant limitation of viral vectors as transducing agents is their entry into cells. For instance, viral vectors have decreased transduction efficiency and gene expression in a variety of cells such as hematopoeitic stem cells. Alternatively, in the case of retroviruses, specific envelop proteins limit the entry of the retrovirus into cells and consequently, the transduction (transfection) efficiency in these cell lines is markedly reduced. There is a need in the art to enhance the entry of viral vectors into cells.

3. SUMMARY OF THE INVENTION

Disclosed herein are novel pharmaceutical agent delivery compositions comprising a novel transport polymer. The transport polymer of the present invention is useful as a system itself or to enhance the transfection efficiency of other transfection systems, such as liposomal transfection systems. The compositions and methods of the invention suitably employ, in addition to the disclosed transport polymer, a variety of transfection systems, including, for example, viral and non-viral delivery systems.

The transport polymer of the invention comprises a linear or branched peptide. Because the peptide-bond linkages of the transport polymer are metabolizable, there is only a low toxicity concern. The linear or branched peptide (i) is comprised of at least 10 amino acid residues, (ii) has from about 5 to 100% histidine residues, (iii) and has from 0 to about 95% non-histidine amino acid residues. The non-histidine amino acid(s) may all be the same amino acid residue or they may be different amino acid residues. The transport polymer may also consist entirely or essentially of the peptide.

The present invention also provides a novel pharmaceutical agent delivery composition comprising: (i) the transport polymer; and (ii) at least one pharmaceutical agent in association with the transport polymer. Components (i) and (ii) are preferably provided in a pharmaceutically suitable carrier.

Also provided is a novel pharmaceutical agent delivery composition comprising: (i) the transport polymer; (ii) at least one intracellular delivery component in association with the transport polymer; and (iii) at least one pharmaceutical agent in stable association with the intracellular delivery component and/or the transport polymer. The components (i), (ii) and (iii) are preferably provided in a pharmaceutically suitable carrier.

In one aspect, the intracellular delivery component of the delivery composition comprises a lipid, preferably a cationic lipid. The cationic lipid may be in the form of a unilamellar or multilamellar liposome.

In another aspect of the invention, the pharmaceutical agent delivery composition comprises one or more helper lipids in addition to a cationic lipid. Such helper lipids may include, for example, diloeleoylphosphatidylethanolamine (DOPE) or cholesterol to enhance transfection. The molar percentage of these helper lipids is preferably between 5 and 50%. In addition, pegylated lipids, which can prolong the in vivo half-life of cationic liposomes, can be present, preferably in molar percentages between 0.05 and 0.5%.

In another aspect of the present invention, the intracellular delivery component comprises a dendrimer. In one embodiment of this type, the intracellular delivery component and the pharmaceutical agent together form a dendrimer-DNA complex In another aspect, the intracellular delivery component comprises a virus particle or a virosome.

The pharmaceutical agent can be a protein, a peptide, nucleic acid, an antisense oligonucleotide, a ribozyme, an RNA-cleaving DNA oligonucleotide, a cancer chemotherapeutic agent, an infectious disease chemotherapeutic agent, a diagnostic agent, or a combination of the above. Where the pharmaceutical agent comprises a nucleic acid, such as a DNA or an RNA molecule, the nucleic acid, in one aspect, is provided as an expression vector; that is, under control of elements which can express the nucleic acid in a host cell. In another aspect, where the nucleic acid is an antisense, ribozyme, or an RNA-cleaving DNA oligonucleotide, an expression vector is not required.

The invention also provides a pharmaceutical agent delivery composition wherein the transport polymer and pharmaceutical agent are associated without the presence of a viral or liposomal carrier. In this embodiment, the transport polymer preferably contains from about 40 to about 300 amino acid residues, and is preferably branched.

In a preferred aspect of the invention, the transport polymer is a linear or branched peptide and has a formula selected from the group consisting of: [K-H-K-H-K-H-K-G-K-H-K-H-K] (SEQ ID NO:1); [K-H-K-H-K-H-K-G-K-H-K-H-K-H-K] (SEQ ID NO:2); [K-H-K-H-K-H-K-G-K-H-K-H-K-H-K-H-K] (SEQ ID NO:3); [K-H-K-H-K-H-K-G-K-H-K-H-K-H-K-H-K-G-K-H-K-H-K-H-K-H-K] (SEQ ID NO:4); [K-H-K-H-H-K-H-H-K-H-H-K-H-H-K-H-H-K-H-K] (SEQ ID NO:5); [K-K-H-H-H-K-H-H-H-K-H-H-H-K-H-H-H-K-K] (SEQ ID NO:6); end-to-end repeats of one or more of the above sequences; the reverse of any of the above sequences; a branched polymer of the formula [K-H-K-H-H-K-H-K-H-K-G-K-H-K-H-K-H-K-H-K]$_{x+1}$K$_x$ where x is equal to 1 to 30; and a branched polymer of the formula [K-H-K-H-H-K-H-H-K-H-H-K-H-H-K-H-H-K-H-K]$_{x+1}$K$_x$ where x is equal to 1 to 30. in these formulas, K is lysine, H is histidine, and G is glycine. In the disclosure, conventional 1-letter amino acids symbols apply.

The invention also provides methods for delivering a pharmaceutical agent to the interior of a cell. In one aspect, the pharmaceutical agent is delivered in vitro to a cell. In another aspect, the pharmaceutical agent is delivered with an ex vivo approach In still another aspect, the pharmaceutical agent is delivered to the cell and/or tissue in vivo. All of these methods comprise the step of administering the pharmaceutical agent delivery composition to deliver the active agent to a cell. The cell may include any animal, plant or bacterial cell that is susceptible to intracellular delivery of the agent using the delivery composition. In one aspect, the cell is selected from the group consisting of lung cells, liver cells, endothelial cells, muscle cells, skin cells, hematopoietic stem cells and tumor cells. The tissue may include any organ or organs from plants or animals.

In the ex vivo gene therapy method, the steps comprise: (i) removing a cell from a subject; (ii) introducing a nucleic acid into the cell by contacting the cell with a pharmaceutical agent delivery composition comprising a nucleic acid active agent; and (iii) reintroducing the cell into the subject. In one aspect, the cell is selected from the group consisting of lung cells, liver cells, endothelial cells, muscle cells, skin cells and hematopoietic stem cells.

4. BRIEF DESCRIPTION OF THE DRAWINGS

FIG. 1 shows the effect of the transport polymer on transfection efficiency. Cells were grown between 60 and 80% confluency forty-eight hours after being plated. Transport polymer was mixed with DNA for 30 minutes. DOTAP liposomes were then added to histidine copolymer. DNA mixture for an additional 30 minutes. Varying amounts of the H-K (19-mer)(SEQ ID NO:3) polymer (0, 1.5, 3, 7.5, 15 nmole), liposome (A-1.5, B-1.0, and C-0.5 μg), and DNA (0.75, 0.5, and 0.25 μg) were mixed. After the complexes were prepared, they were diluted in OptiM and added to the cells for 4 hours. Forty-eight hours later, the luciferase activity was measured.

Figure 2:
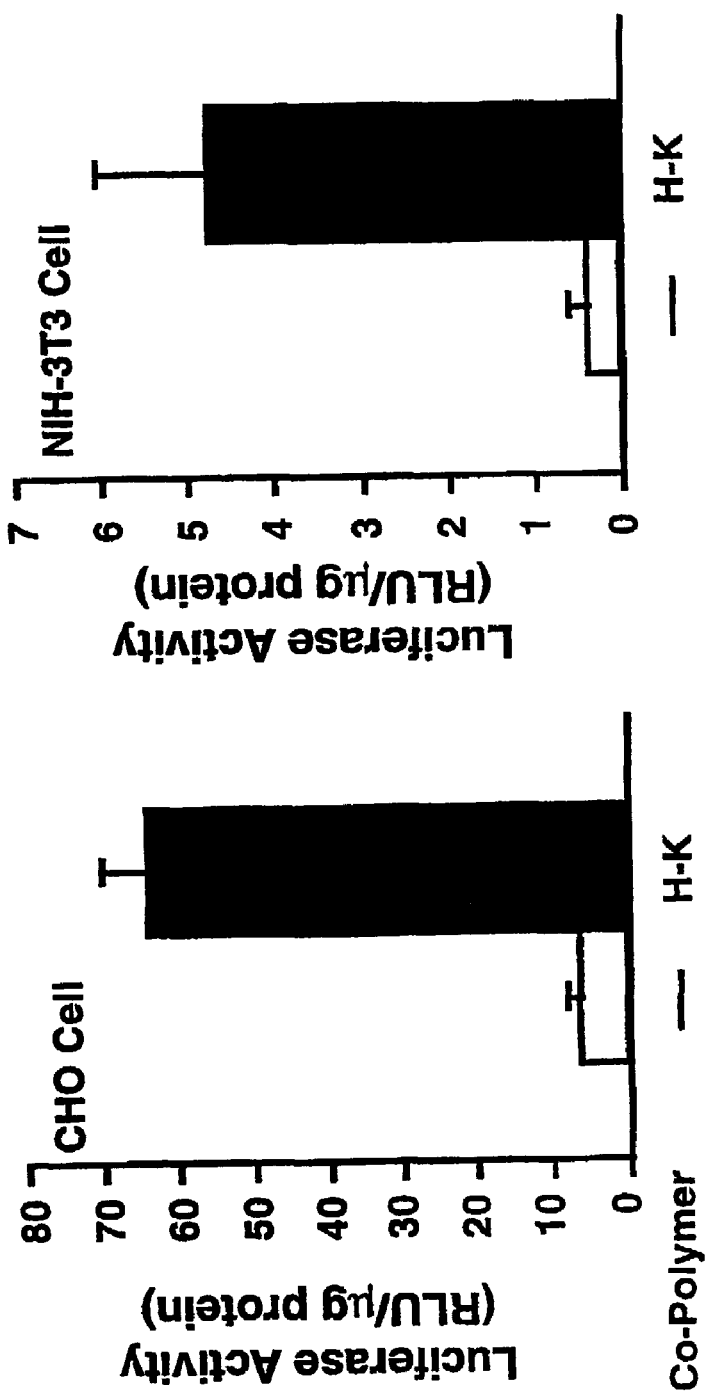

FIG. 2. Enhanced Transfection with Histidine Copolymer in CHO and NIH-3T3 Cells. H-K (19-mer) (SEQ ID NO:3) polymer (7.5 nmole) was initially mixed with 0.75 μg of DNA before adding 1.5 μg of liposomes. Transfection efficiency of liposome: DNA (PCI-Luc) complex vs. H-K: liposome: DNA in CHO $p<0.0002$) and NIH3T3 ($p<0.02$) cells in the absence of serum.

Figure 3:
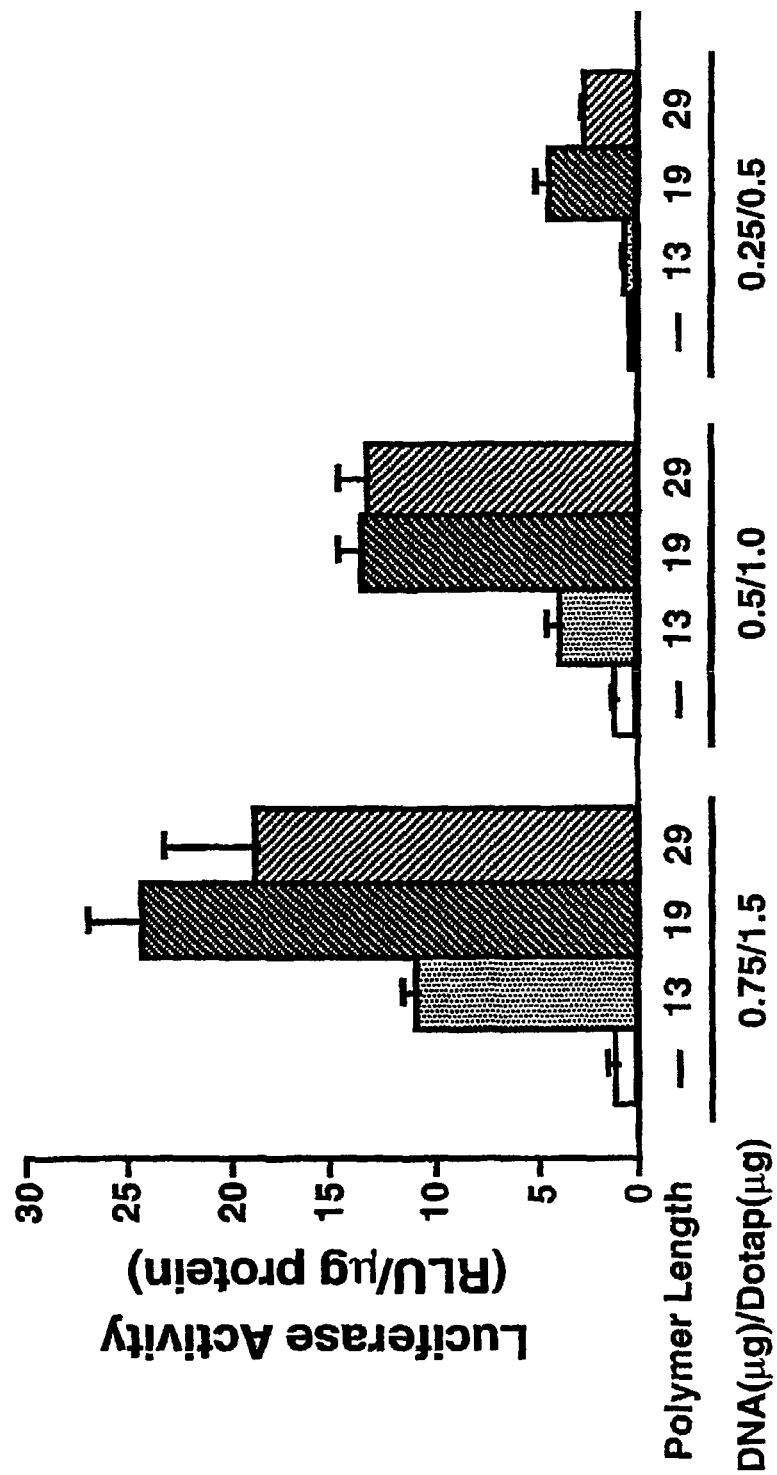

FIG. 3. Transport polymer length can affect the transfection efficiency. Transfection conditions are similar as previously described except that different lengths of the H-K polymer (13mer [SEQ ID NO:1], 19mer [SEQ ID NO:3], and 29mer [SEQ ID NO: 4]) were initially mixed with the DNA before adding liposomes. 7.5 nmole of polymer was mixed with the indicated amounts of liposome and DNA. H-K(13-mer), H-K(19-mer), H-K(29-mer) vs. no polymer, $p<0.05$; H-K(13-mer) vs. no polymer, at DNA concentrations of 0.75 and 0.5 μg, $p<0.05$; H-K(19-mer), H-K(29-mer) vs. H-K(13-mer), $p<0.05$.

Figure 4:
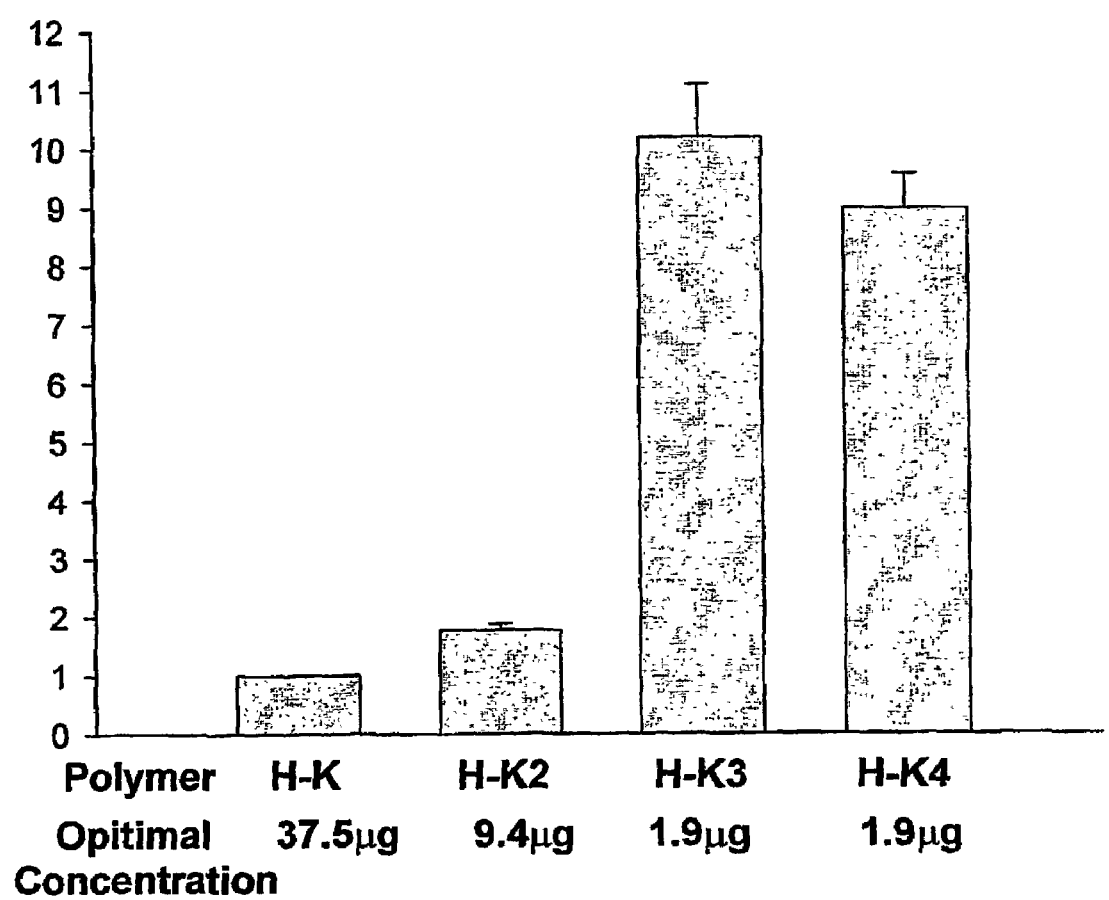

FIG. 4. Branching of the transport polymer can increase transfection efficiency. Optimal dose of the various branched H-K polymers are designated in the figure. To determine the optimal dose of polymer, we varied the H-K polymer and the branched H-K polymers from 0.3 μg to 75 μg. The polymers were mixed with 0.75 μg of DNA before adding 0.5 μg of liposomes. The fold-increase in transfection due to the branching of H-K2b ("H-K2"), H-K3b ("H-K3"), and H-K4b ("H-K4") polymers are compared to the H-K polymer. H-K3b or H-K4b vs H-K, $p<0.05$.

Figure 5:
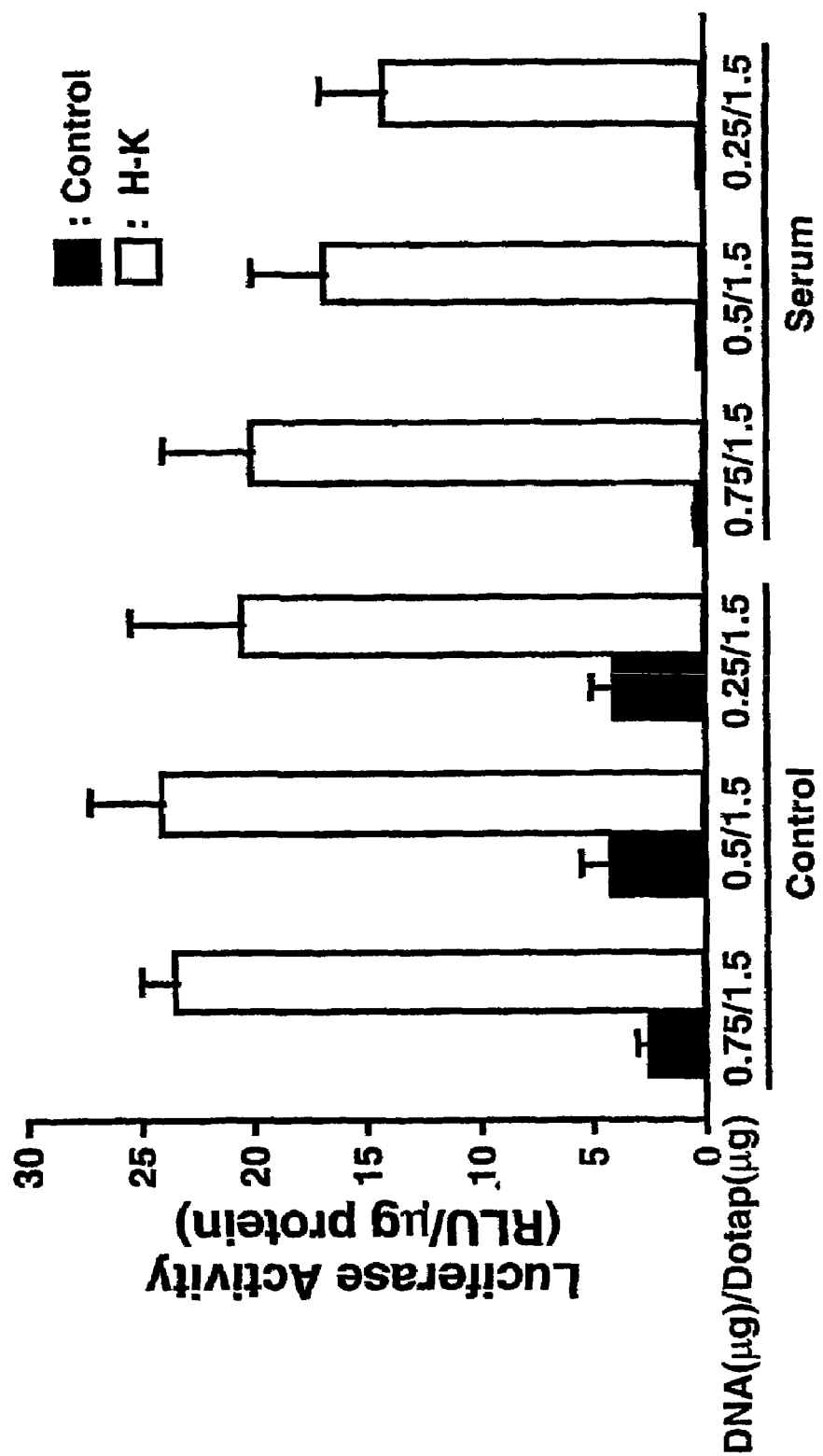

FIG. 5. H-K Transport Polymer Can Enhance Transfection Efficiency in the Presence of Serum. H-K: liposome: PCI-Luc and liposome: PCI-Luc complexes were prepared as described in section 6.2. The complexes were diluted in either OptiM(□) or OptiM with 10% serum (■) and added to the cells for 4 hours. Luciferase activity was measured 48 hours later. H-K: liposome: PCI-Luc vs. liposome: PCI-Luc without serum, $p<0.01$; H-K: liposome: PCI-Luc vs. liposome: PCI-Luc with serum, $p<0.002$.

Figure 6:
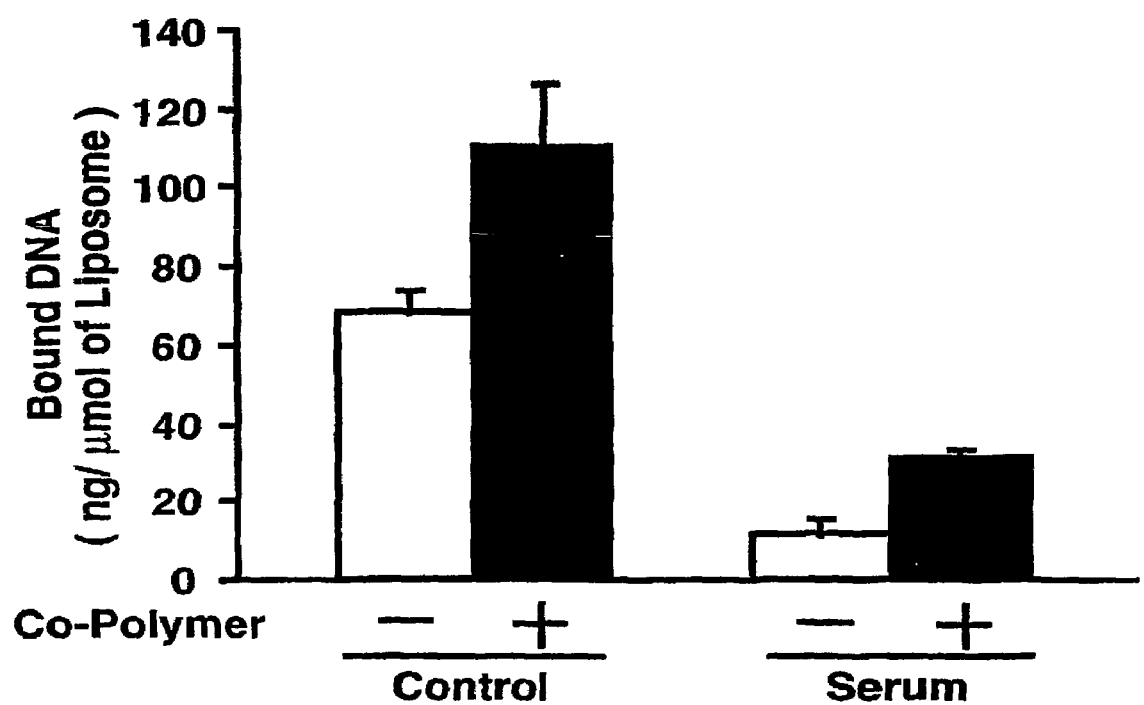

FIG. 6. DNA Binding to Cationic Liposomes in the Presence of H-K Transport Polymer. Histidine copolymer increased DNA binding to liposomes from 1.5 to 3-fold (over liposomes alone) in the presence or absence of serum.

Figure 7:
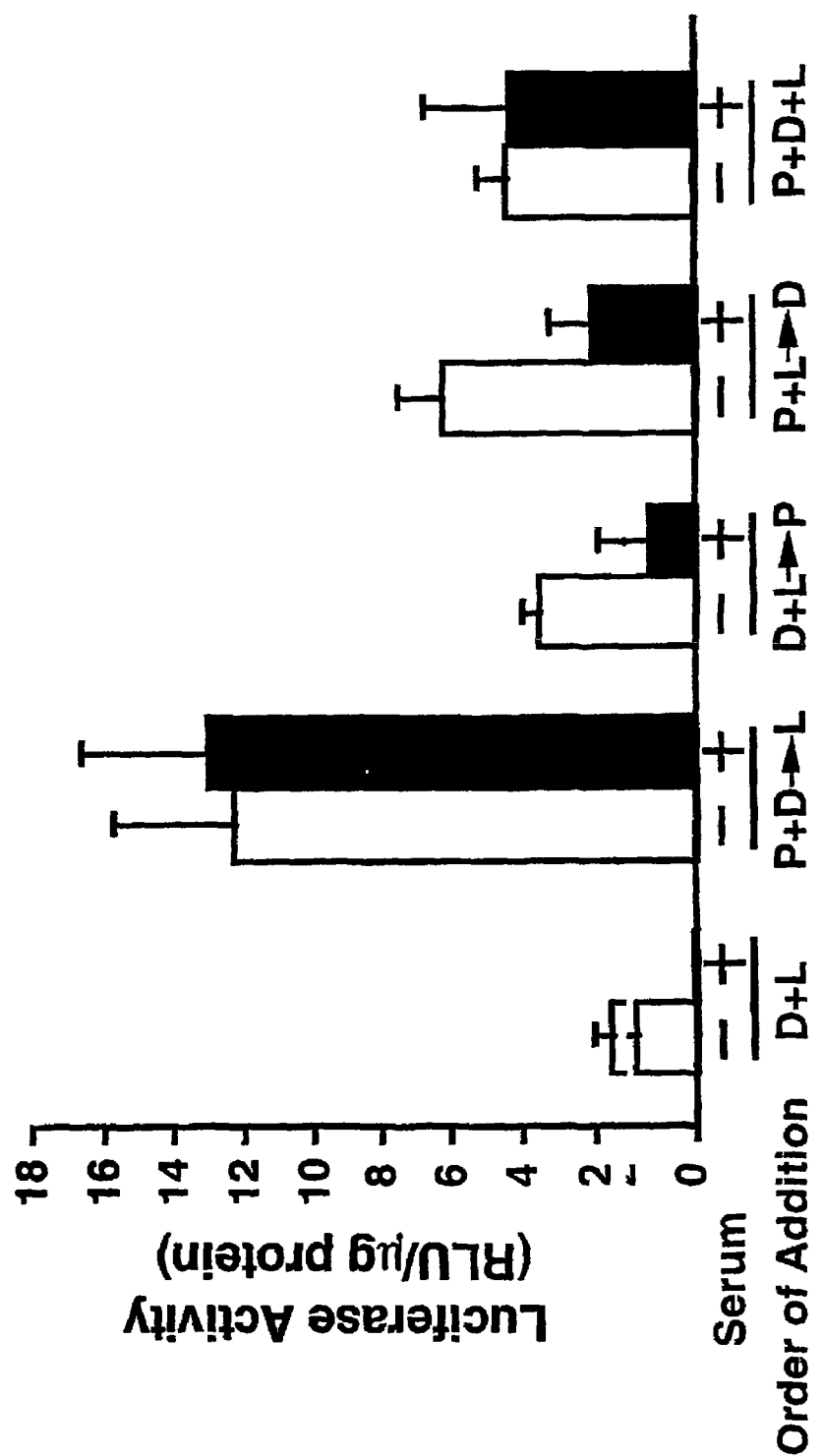

FIG. 7. Order of Addition of Delivery Components Affects Transfection Efficiency. The following order was used to prepare the transfection complexes: A) DNA (D)+ liposomes (L), B) DNA+histidine copolymer (P) for 30 minutes, then liposomes added for 30 minutes, C) DNA+ liposome for 30 minutes, followed by histidine copolymer for 30 minutes, D) histidine copolymer and liposomes were mixed with each other for 30 minutes before adding DNA, and E) histidine copolymer, liposomes, and DNA were mixed simultaneously. After the complexes were prepared, they were added to the cells in the presence or absence of 10% serum.

Figure 8:
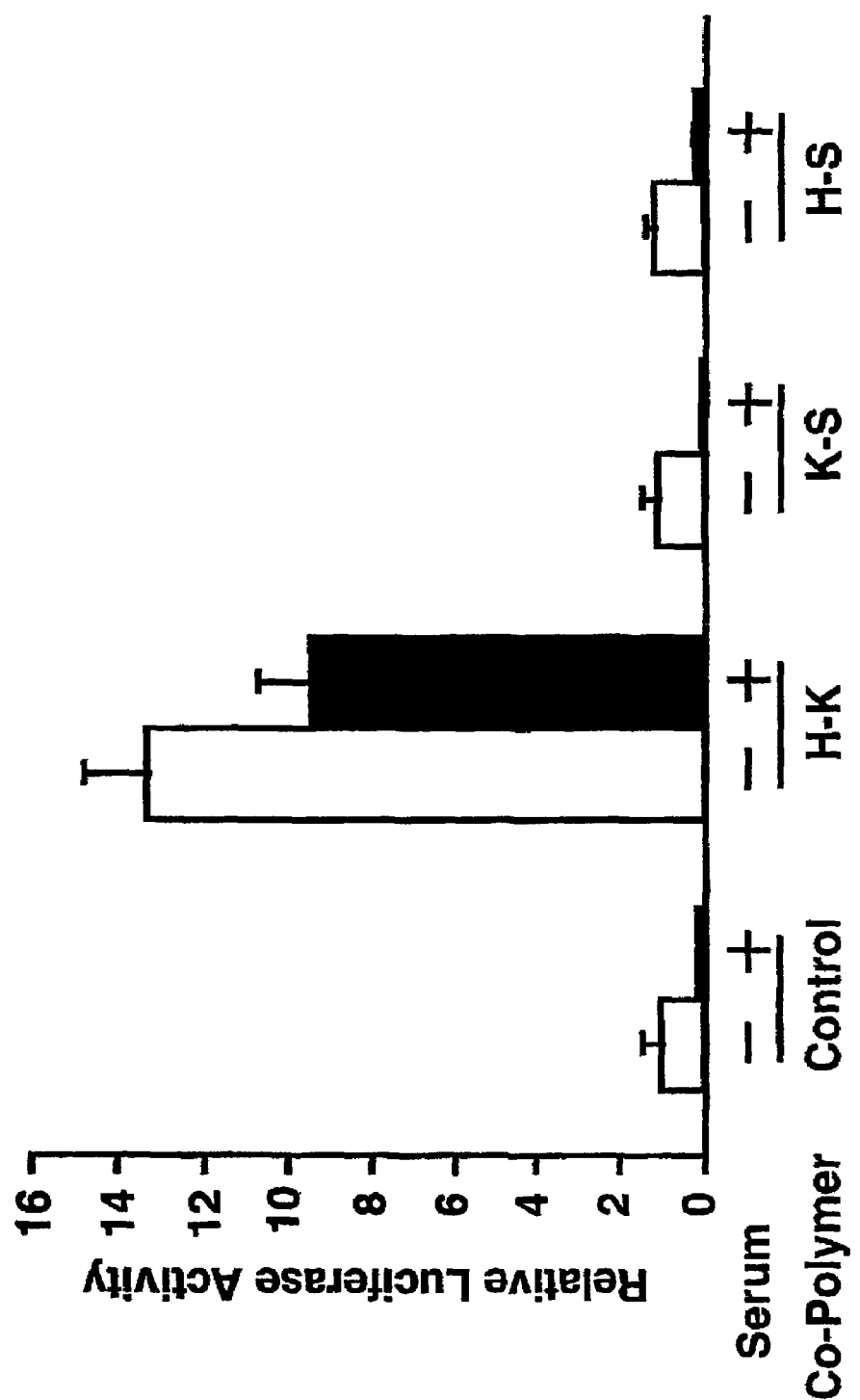

FIG. 8. Comparison of the H-K, S-K, and H-S Copolymers on Transfection Efficiency. Polymer: liposome:PCI-Luc and liposome: PCI-Luc were prepared as described in section 6.2. After the complexes were prepared, they were added to the cells in the presence or absence of 10% serum. H-K vs. other treatment groups without serum, $p<0.01$; H-K vs. other polymers with serum, $p<0.001$.

Figure 9:
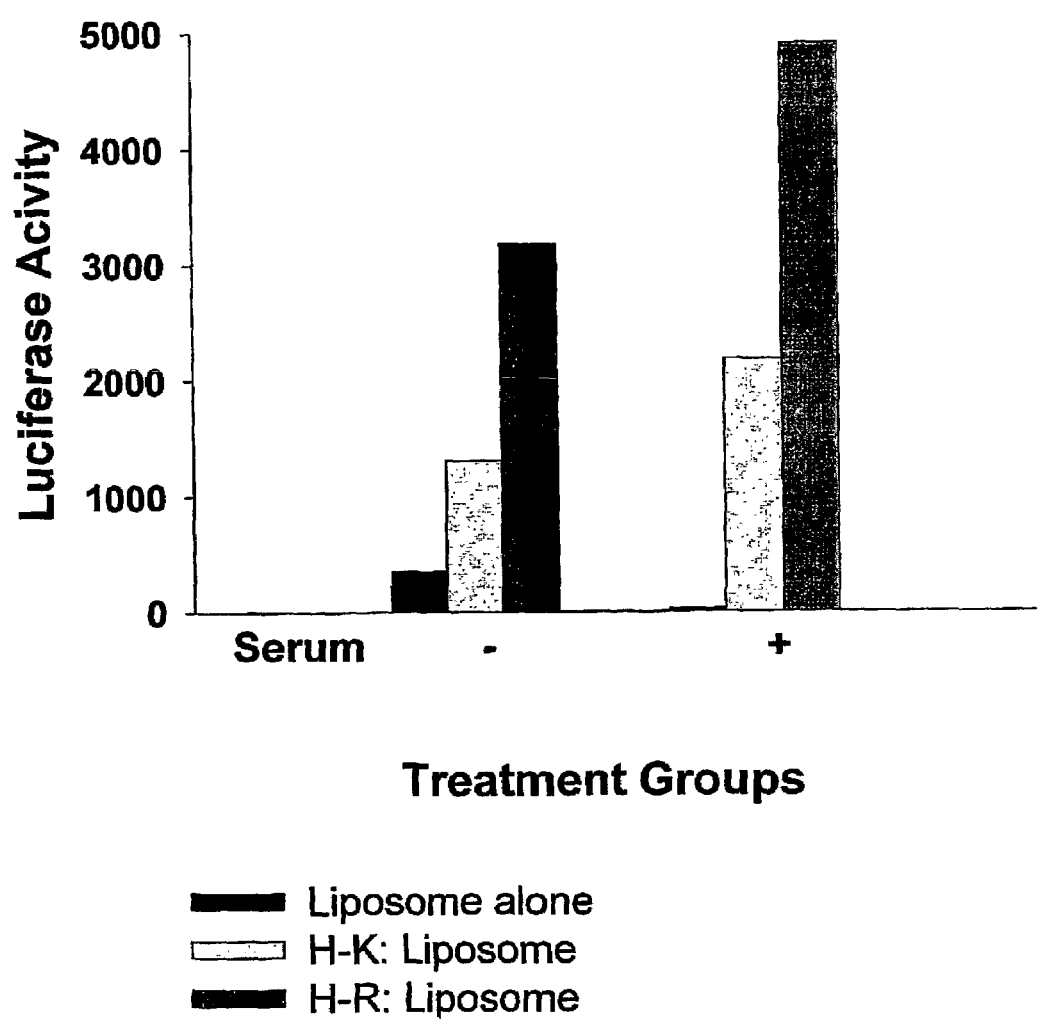

FIG. 9. Comparison of arginine-histidine copolymer (H-R) as compared to H-K in enhancing transfection efficiency.

Figure 10:
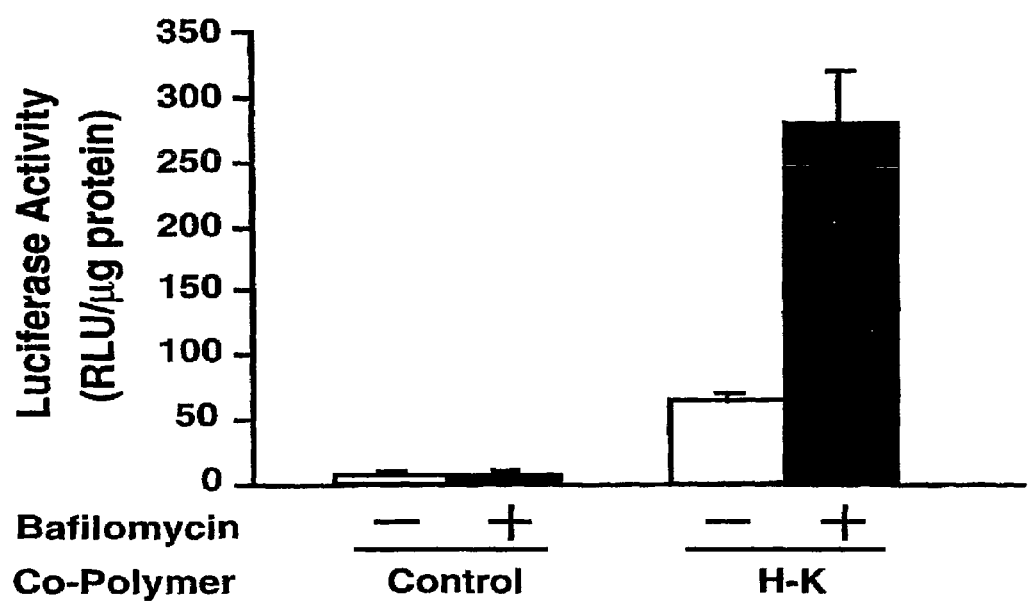

FIG. 10. The effect of bafilomycin on luciferase activity using complex with or without histidine copolymer in CHO cells. H-K: liposome: PCI-Luc and liposome: PCI-Luc complexes were prepared as described in section 6.2. Cells were treated as in FIG. 1 with 10 ng/ml bafilomycin added to cells at the same time as transfection agents. H-K: liposome: PCI-Luc with Bafilomycin vs. H-K: liposome: PCI-Luc, $p<0.002$.

Figure 11:
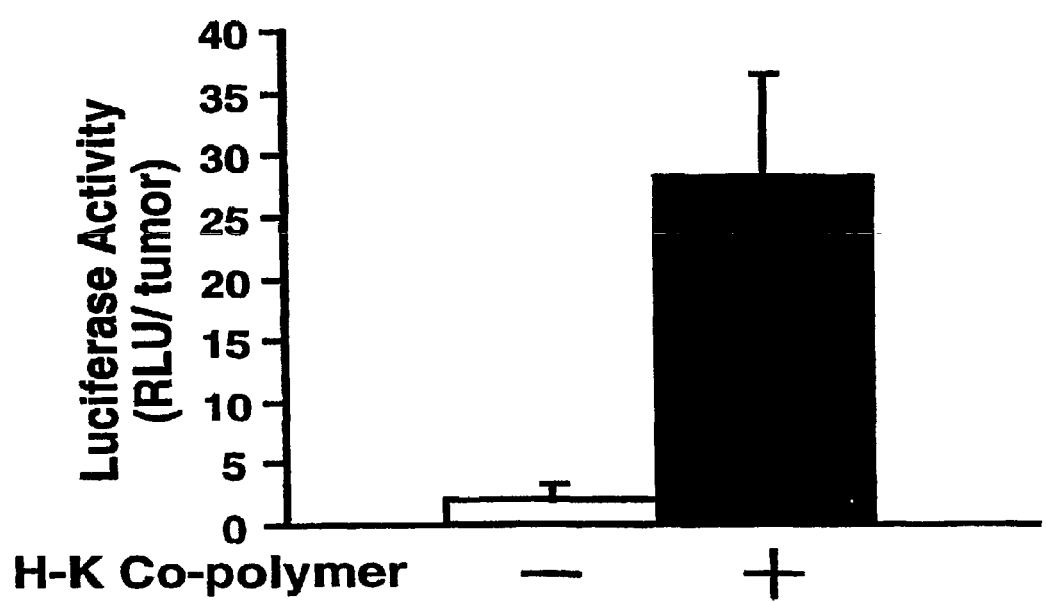

FIG. 11. Histidine Transport Polymer Increases in vivo Transfection Efficiency. One week after injection of MDA-MB-435 cells bilaterally into the mammary fat pads of nude mice, and tumors were visibly present, complexes were injected into the tumors. The liposome: PCI-Luc complex was injected into one tumor whereas the H-K: liposome: PCI-Luc complex was injected into the contralateral tumor., Each tumor was injected with 25 μl of a solution containing 42 nmole of liposomes, 22 nmole of the histidine copolymer, and 2.34 μg of DNA Twenty-four hours after injection, the luciferase values were measured. H-K: liposome: PCI-Luc vs. liposome: PCI-Luc complexes, $p<0.002$. See section 6.2 for further details on preparation.

Figure 12:
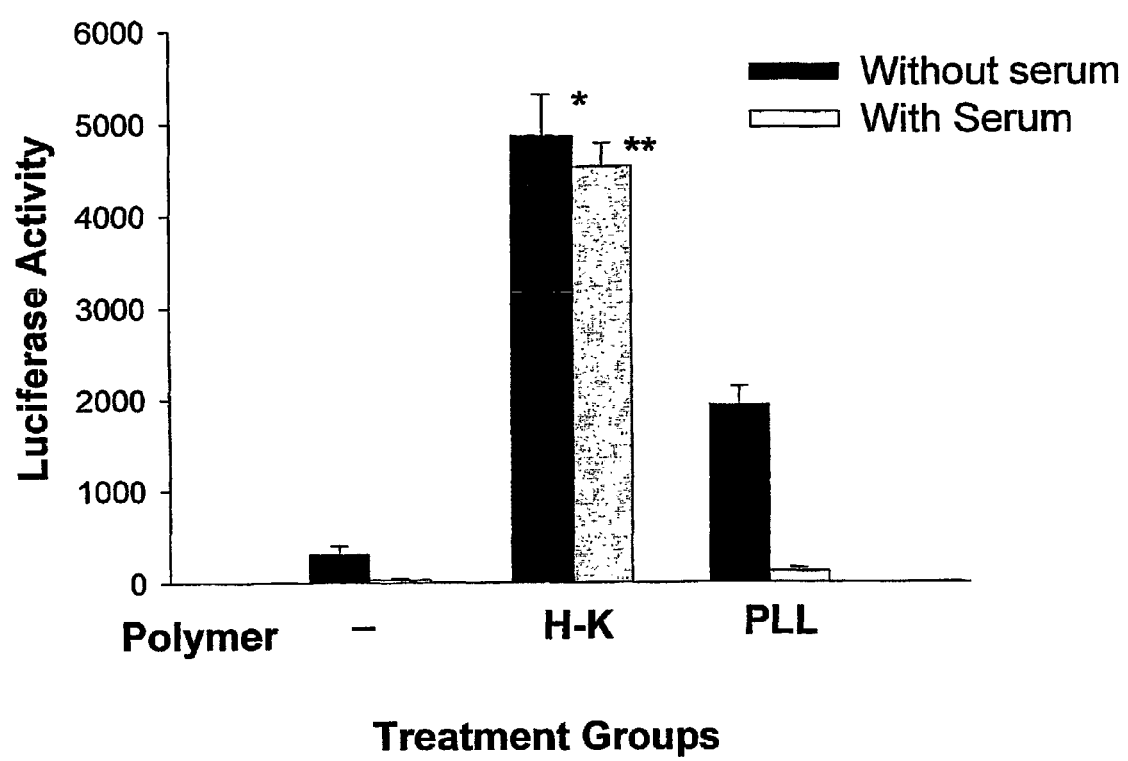

FIG. 12. Comparison of H-K polymer with poly-L-lysine polymer, with and without serum. Compared to poly-L-lysine (PLL), the H-K polymer enhances the transfection efficiency of PCI-Luc in MDA-MB435 cells. The H-K or PLL polymer (25 μg) was initially mixed with 0.75 μg of DNA before adding 1.5 μg of liposomes. H-K vs. poly-L-lysine without serum, $p<0.005$; H-K vs. poly-L-lysine with serum, $p<0.0001$.

Figure 13:
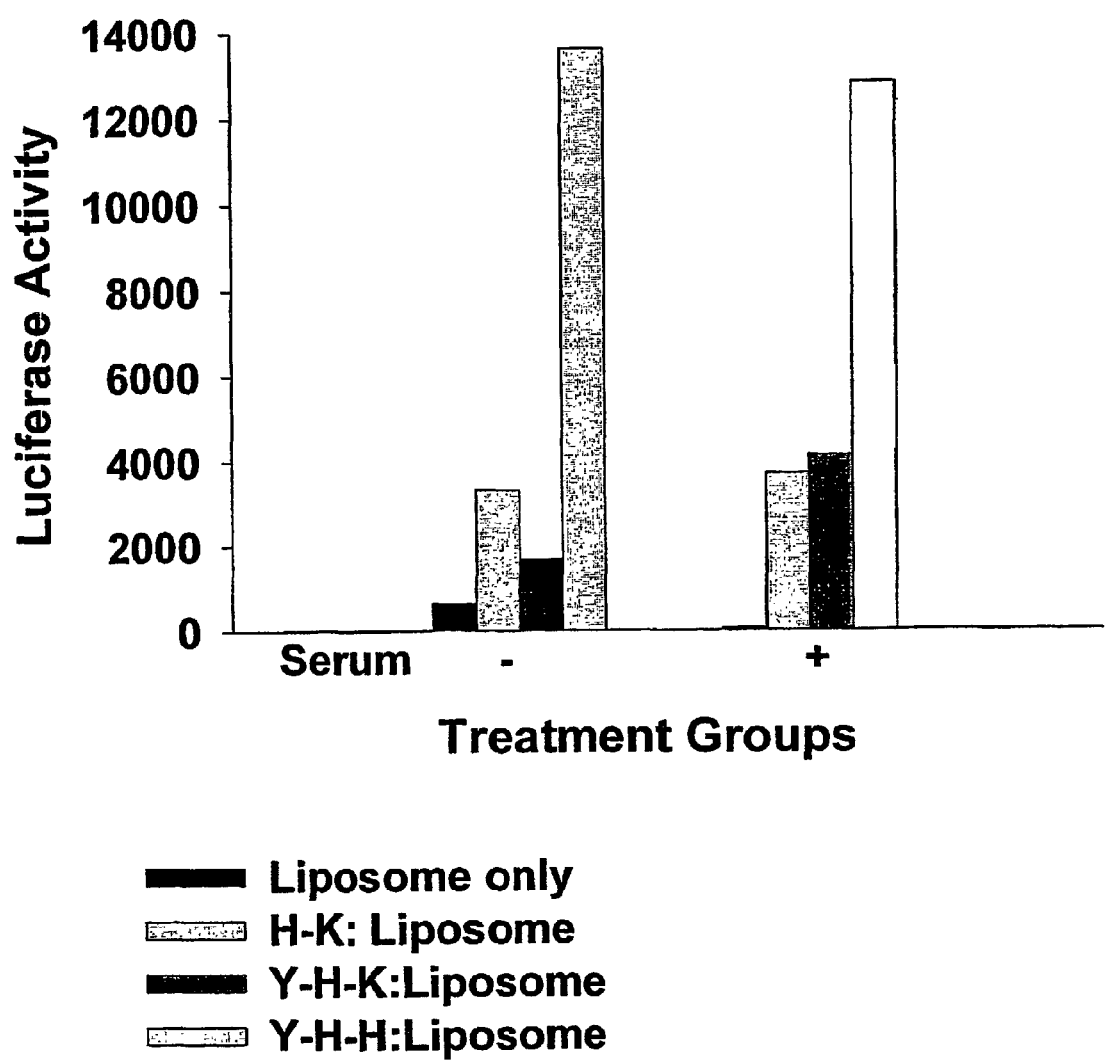

FIG. 13. The order of the H-K amino acids can affect transfection efficiency. Polymers H-K (SEQ ID NO:3), Y-HK (SEQ ID NO:7), and Y-HH (SEQ ID NO:8) were mixed initially with DNA and then liposomes were added as previously described. Compared to H-K or Y-HK, the Y-HH polymer significantly enhanced the uptake of liposomes in the presence or absence of serum. Since the Y component (Y-G-R-K-K-R-R-Q-R-R-R) was present in both the Y-HK and the Y-HH polymers, the sequence in the Y-HH polymer that enhanced uptake is the HH component (H-H-K-H-H-K-H-H-K-H-H-K-H-H-K).

Figure 14:
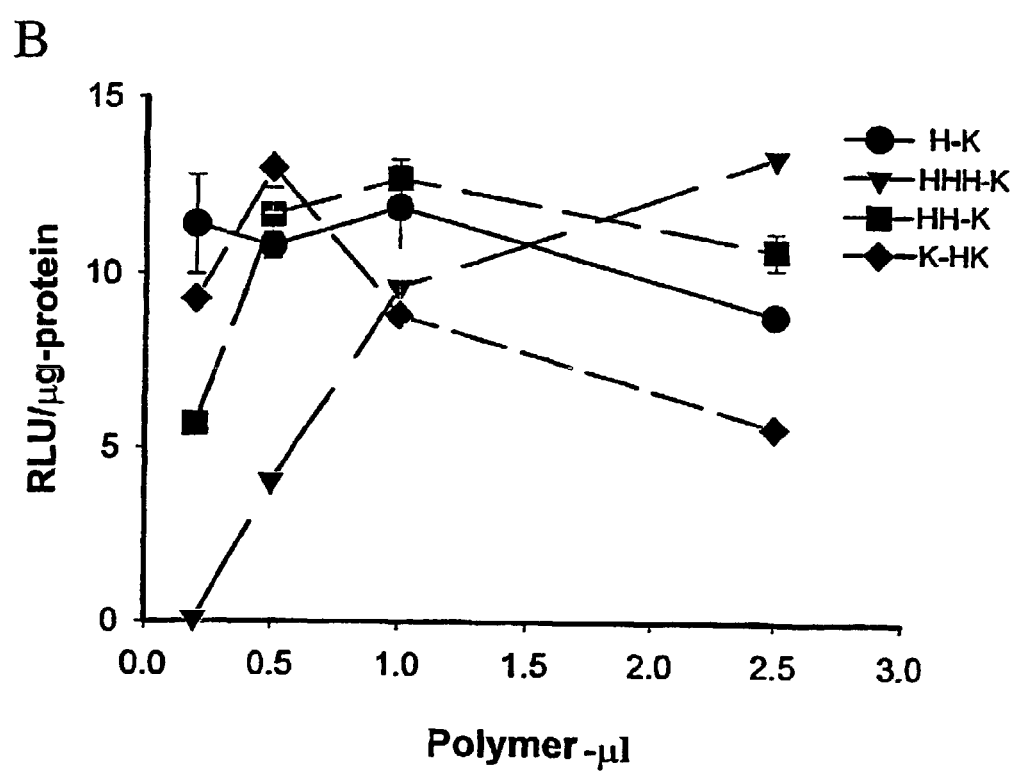

FIG. 14 Comparison of the effect of histidine order and histidine copolymer concentration on the ability of a polymer:DNA:liposome complex to stimulate transfection efficiency. Four copolymers, H-K(19-mer) (SEQ ID NO:3), HHH-K (SEQ ID NO:6), HH-K (SEQ ID NO:5), and K-HK (SEQ ID NO:9) were compared. At the highest concentration of polymer used, the HHH-K polymer was the most effective of the four at transfecting DNA when used in combination with liposomes; however, at lower concentrations the HHH-K polymer is not as effective as the other three polymers tested. One microliter of polymer solution equates to 15 μg.

Figure 15:
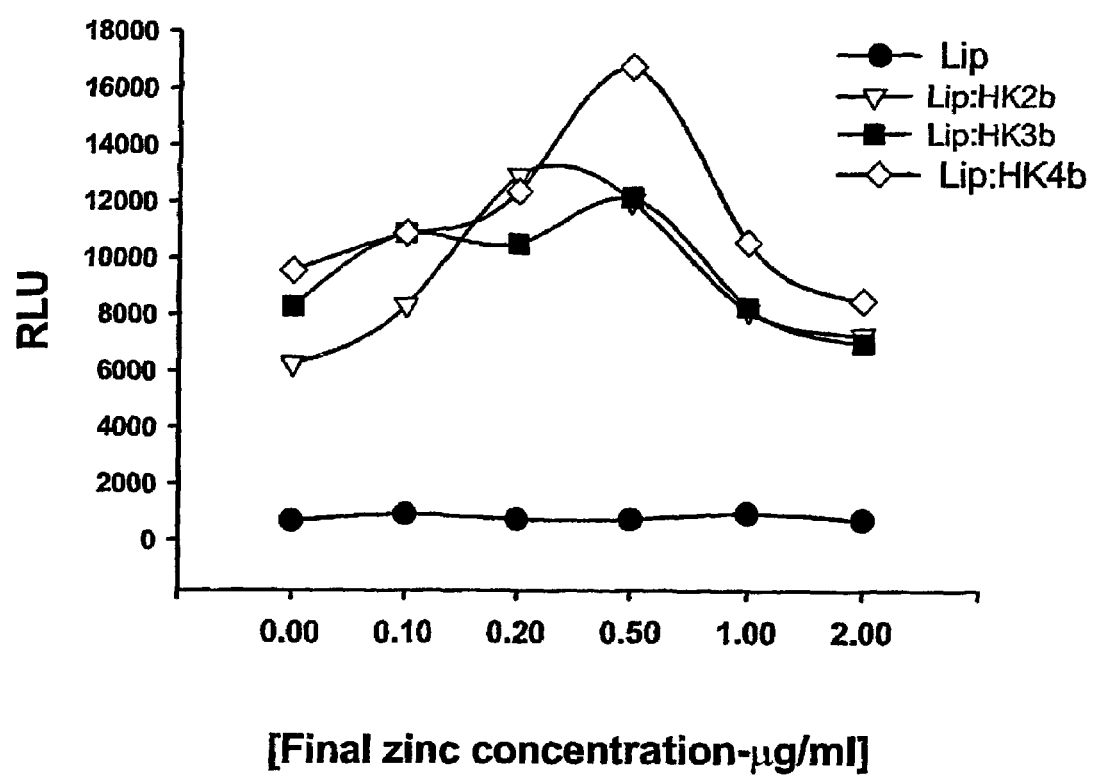

FIG. 15. The effect of adding transition metals on the transfection efficiency of a polymer:DNA complex. 0.25 μg H-K2b, 0.125 μg H-K3b, or 0.125 μg H-K4b were initially mixed with 0.75 μg DNA. After 30 minutes, cationic liposomes were added for 30 minutes. $Zn^{2+}$ was then added in an amount ranging from 0 to 2.00 μg/ml. As a control, various amounts of zinc were added to the liposome:DNA complex. The addition of zinc can enhance transfection efficiency of polymer:liposome:DNA complexes.

Figure 16:
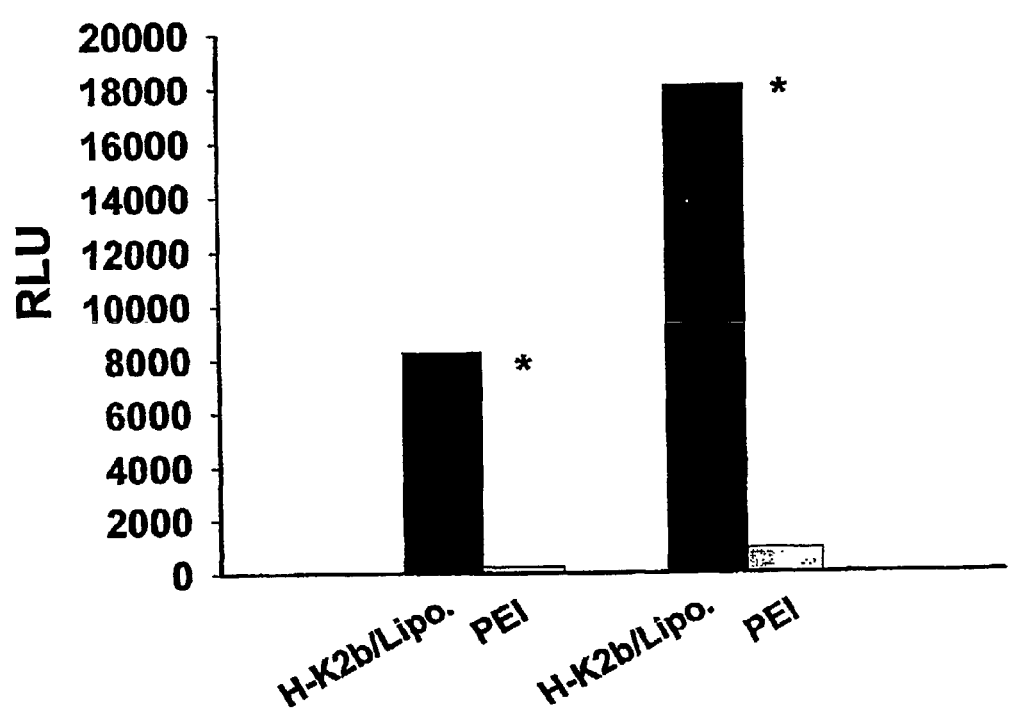

FIG. 16. Transfecton of MDA-MB-435 cells with either PEI or a H-K2b:liposome carrier. PEI and an H-K2b:liposome carrier were compared for their ability to transfect MDA-MB435 cells in the presence or absence of serum Forty-eight hours after transfection, luciferase activity was determined. The combination of H-K2b and liposomes significantly improved transfection compared to PEI (* p<0.01, H-K4b/liposome vs. PEI).

Figure 17:
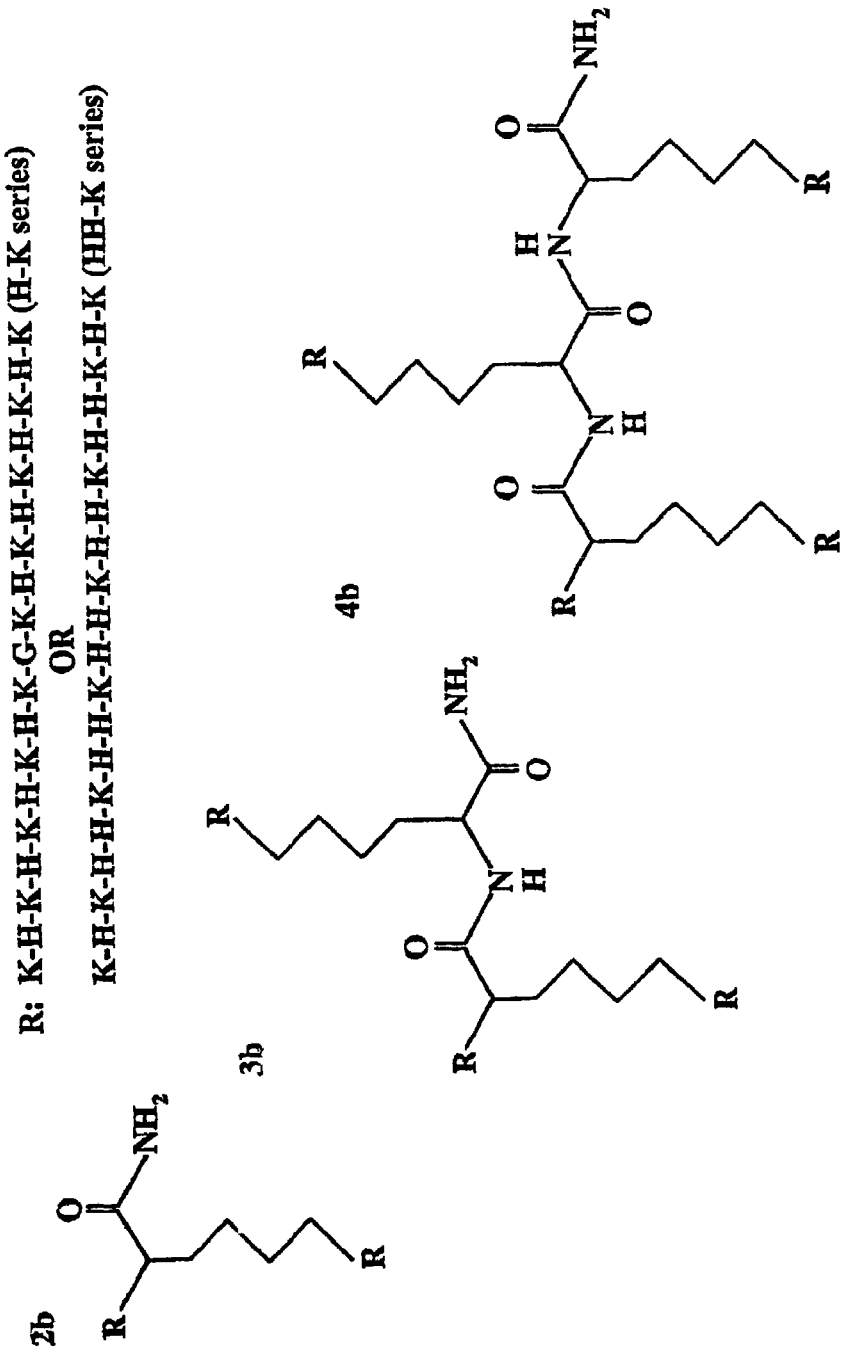

FIG. 17. Schematic structure of exemplary histidine-lysine branched transport polymers. In one aspect of the invention, branched polymers consist of polymers emanating from a lysine core. The branches of the polymer can emanate from non-consecutive lysines, or as depicted here, from consecutive lysines. R represents K-H-K-H-K-H-K-H-K-G-K-H-K-H-K-H-K-H-K (SEQ ID NO:3) for the H-K series of branched polymers and K-H-K-H-H-K-H-H-K-H-H-K-H-H-K-H-H-K-H-K (SEQ ID NO:5) for the HH-K series of branched polymers.

Figure 18:
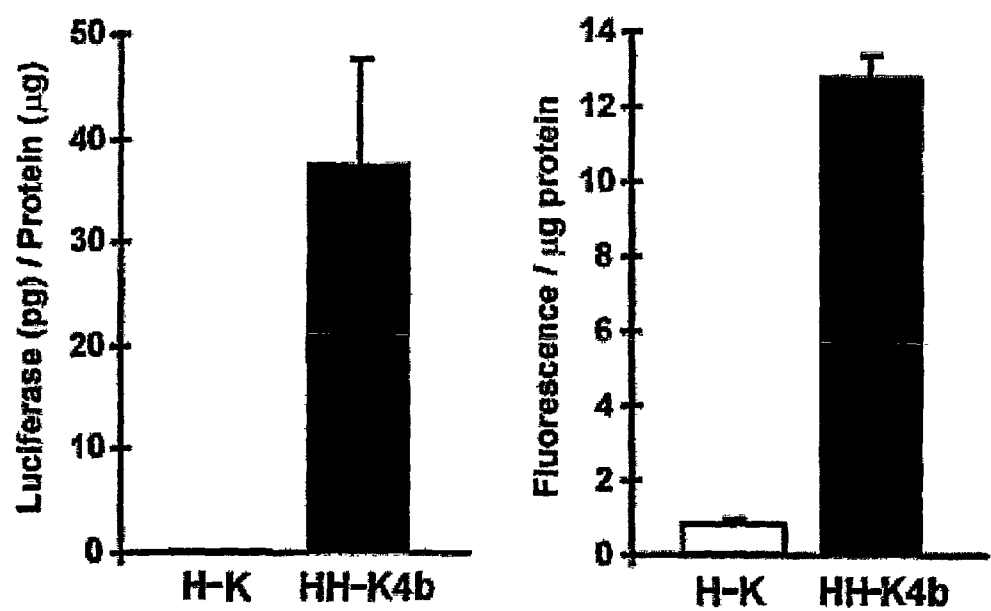

FIG. 18. The branched transport polymer can increase transfection efficiency of a plasmid and uptake of oligonucleotide in the absence of liposome. a) 7.5 nmol of H-K or 0.375 nmol of HH-K4b was mixed with PCI-Luc, and luciferase activity was measured as described in section 6.2. The branched HH-K4b polymer showed better transfection efficiency than the linear H-K polymer (*p<0.05, HH-K4b vs. H-K). b) The branched HH-K4b polymer significantly enhanced uptake of oligonucleotides when compared to a linear HK polymer: oligonucleotides complex (*p<0.05, Mann-Whitney Rank-Sum Test). The same amount of H-K or HH-K4b was mixed with 0.75 μg of a 5'-end fluorescein-labeled randomly generated oligonucleotide (32-mer) for 30 minutes. This complex was added to the MDA-MB-435 cells for 4 hour incubation. 24 hours later, the cells were then washed, and measured by CytoFluor fluorescence Measurement System.

5. DETAILED DESCRIPTION OF THE INVENTION

5.1 Definitions

The term "amino acid" is inclusive of the 20 common amino acids, as well as "nonstandard amino acids," for example, D-amino acids and chemically (or biologically) produced derivatives of "common" amino acids.

A compound is "associated with" a second compound if the two compounds have formed a complex as a result of covalent or non-covalent interactions between the two compounds.

The term "copolymer" refers to a polymer that contains two or more types of units, regardless of the arrangement of units along the chain (random, alternating, block, graft), and regardless of its molecular structure (linear or branched). The term "histidine copolymer" means that the copolymer comprises histidine as one of its unit types. The term "transport polymer" means a polymer comprising the histidine copolymer of the invention.

The term "peptide" is inclusive of both straight and branched amino acid chains, as well as cyclic amino acid chains, which comprise at least 2 amino acid residues. The term "polypeptide" is inclusive of both straight and branched amino acid chains, as well as cyclic amino acid chains, which comprise at least 2 amino acid residues. The terms "peptide" and "polypeptide" are used interchangeably herein.

The term "branched peptide" is inclusive of any peptide having at least one amino acid covalently attached to a side-group of another amino acid. An amino acid having a side-group by which a peptide has attached is referred to as a "branching amino acid."

The term "lipid" includes any chemical species having a hydrophobic and a hydrophilic part such as to enable the chemical species to become incorporated into a micelle or liposome. Hydrophilic characteristics typically derive from the presence of phosphate, carboxylic, sulfato, amino, sulfhydryl, nitro, and other like groups. Hydrophobicity is conferred by cholesterol and derivatives and by the inclusion of groups that include, but are not limited to, long chain saturated and unsaturated aliphatic hydrocarbon groups and such groups substituted by one or more aromatic, cycloaliphatic or heterocyclic group(s).

The term "non-cationic lipid" refers to any of a number of lipid species that exist either in an uncharged form a neutral zwitterionic form, or an anionic form at physiological pH. Such lipids include, for example diacylphosphatidylcholine, diacylphosphatidylethanolamine, ceramide, sphingomyelin, cephalin, cardiolipin, cerebrosides, DOPE, and cholesterol.

The term "cationic lipid" refers to any of a number of lipid species which carries a net positive charge. Such lipids include, but are not limited to, DODAC, DOTMA, DDAB, DOSPER, DOSPA, DOTAP, DC-Chol and DMRIE. Additionally, a number of commercial preparations of cationic lipids are available which can be used in the invention. These include, for example, LIPOFECTIN Registered™ (commercially available cationic liposomes comprising DOTMA and DOPE, from GIBCO/BRL, Grand Island, N.Y., USA); LIPOFECTAMINE Registered™ (commercially available cationic liposomes comprising DOSPA and DOPE, from GIBCO/BRL); and TRANSFECTAM Registered™ (commercially available cationic liposomes comprising DOGS from Promega Corp., Madison, Wis., USA).

A "pharmaceutical agent" includes any therapeutic agent useful in preventing, delaying or reducing the severity of the onset of a disease, or in reducing the severity of an ongoing disease, or in enhancing normal physiological functioning, as well as diagnostic agents, for example, a marker gene (GFP, luciferase). A "pharmaceutical agent" may consist of one or more therapeutic agents, one or more diagnostic agents, or a combination of one or more therapeutic and one or more diagnostic agents.

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

As used herein, a "pharmaceutically acceptable" component (such as a salt, carrier, excipient or diluent) of a pharmaceutical agent delivery composition according to the present invention is a component which (1) is compatible with the other ingredients of the delivery composition in that it can be included in the delivery composition without eliminating the capacity of the composition to deliver the pharmaceutical agent; and (2) where the delivery composition is intended for therapeutic uses, is suitable for use with an animal (e.g., a human) without undue adverse side effects, such as toxicity, irritation, and allergic response. Side effects are "undue" when their risk outweighs the benefit provided by the pharmaceutical agent.

The word "transfect" is broadly used herein to refer to introduction of an exogenous compound, such as a polynucleotide sequence, into a prokaryotic or eukaryotic cell; the tern includes, without limitation, introduction of an exogenous nucleic acid into a cell, which may result in a permanent or temporary alteration of genotype or in an immortal or non-immortal cell line.

As used herein, the term "physiologic pH" is defined as a pH between about 7.2 and about 7.5.

The term "in vivo" includes therapy based on injection, whether intravenous or local (e.g., intratumoral, intramuscular, subcutaneous, intratracheal, intravenous, injection into organ or airway directly, injection into vessels of the organ, or aerosolized into airways). The term "in vivo" also includes therapy based on electroporation of tumor, tissue, or organ.

5.2 Pharmaceutical Agent Delivery Compositions

In one embodiment, the pharmaceutical agent delivery composition comprises: (i) a transport polymer, and (ii) at least one pharmaceutical agent in association with the transport polymer. Components (i) and (ii) are preferably provided in a suitable carrier, such as a pharmaceutically acceptable carrier. In this embodiment, there is preferably no viral or liposomal component, and the transport polymer preferably comprises a branched histidine copolymer. In this embodiment, it is preferred that the complex formed by the transport polymer and the pharmaceutical agent be stable at a pH between 5.0 and 7.4.

In another embodiment, the pharmaceutical agent delivery composition comprises: (i) the transport polymer, (ii) at least one intracellular delivery component in association with the transport polymer, and (iii) at least one pharmaceutical agent in association with the intracellular delivery component and/or the transport polymer. A preferred method of making this embodiment is by combining (i) and (ii) for a time sufficient for the transport polymer and the pharmaceutical agent to associate into a stable complex. Where the pharmaceutical agent is nucleic acid, the intracellular delivery component preferably comprises lipids, and more preferably, cationic lipids. The components (i), (ii) and (iii) are also preferably provided in a suitable carrier, such as a pharmaceutically acceptable carrier.

5.2.1 Transport Polymer

In the above embodiment, the transport polymer comprises a straight or branched polypeptide comprising histidine and non-histidine residues. The non-histidine residues may be the same or different.

The polypeptide preferably contains about 10 to about 300 amino acid residues, more preferably 10 to 150 amino acid residues, still more preferably from 10 to 100 amino acid residues. When the polypeptide is linear, the preferred length is generally less than about 50 amino acid residues. Where the polypeptide is branched, the preferred number of residues is greater than about 40, preferably from about 40 to about 300 amino acid residues. Where the pharmaceutical agent delivery composition does not contain an intracellular delivery component, the polypeptide is (i) preferably branched and (ii) comprised of at least about 40 amino acid residues, preferably from about 40 to about 300 amino acid residues.

In a preferred form, the transport polymer comprises from about 5 to 100% histidine residues, more preferably from about 10 to 100% histidine residues, still more preferably from about 20 to about 80% histidine residues, and still more preferably from about 40 to about 60% histidine residues. The histidine residues of the polypeptide are preferably uniformly interspersed into the transport polymer structure. The amino acids of the transport polymer are preferably distributed such that there is at least one histidine residue in every subsegment of 2 to 5 amino acid residues, more preferably at least one histidine residue in every subsegment of 2 to 4 amino acid residues, still more preferably at least one histidine residue in every subsegment of 2 to 3 amino acids, and most preferably about one histidine residue in every subsegment of 2 amino acids. In another aspect of the invention, the amino acids are distributed such that there is 1 to 5 histidine residues in every subsegment of 2 to 5 amino acid residues, more preferably 1 to 4 histidine residues in every subsegment of 2 to 4 amino acid residues, still more preferably 1 to 3 histidine residues in every subsegment of 2 to 3 amino acids, and ideally 1 to 2 histidine residues in every subsegment of 2 amino acids.

The transport polymer may contain from 0 to about 95% non-histidine amino acid residues, more preferably from about 10 to about 90% non-histidine residues, still more preferably from about 20 to about 80% non-histidine residues, and still more preferably from about 40 to about 60% non-histidine residues. The non-histidine residues are preferably distributed such that there is an average of at least one non-histidine residue in every subsegment of 2 to 7 amino acid residues The non-histidine amino acid(s) may all be the same amino acid residue or they may be different amino acid residues. Where the pharmaceutical agent has an overall negative charge (for example, nucleic acid) the non-histidine amino acid(s) are preferably selected from the group consisting of amino acids with a side-group that carries a positive charge at physiological pH (for example, lysine and arginine). More preferably, the non-histidine amino acid(s) comprise lysine residues. In one aspect of the invention, the non-histidine amino acid(s) are all lysine.

The non-histidine amino acid(s) are also suitably selected from the group consisting of amino acids with a side-group that carries a negative charge at physiological pH (for example, aspartic acid and glutamic acid) as well as amino acids that are neutral at physiological pH (for example, glycine and serine).

Preferably, non-histidine amino acid(s) are selected so as to tailor the transport polymer to the particular pharmaceutical agent and the intended method of association. Thus, where the pharmaceutical agent is a nucleic acid (overall negative charge) and non-covalent association with the transport polymer is desired, the non-histidine amino acid(s) are preferably selected from the group consisting of amino acids with a side-group that carries a positive charge at physiological pH. In contrast, if the pharmaceutical delivery composition is comprised of covalently associated transport polymer and pharmaceutical agent, the selection of non-histidine amino acids is less restricted.

In a preferred aspect of the invention, the transport polymer is a linear or branched polypeptide and has a formula selected from the group consisting of: [K-H-K-H-K-H-K-G-K-H-K-H-K] (SEQ ID NO:1); [K-H-K-H-K-H-K-G-K-H-K-H-K-H-K] (SEQ ID NO:2);, [K-H-K-H-K-H-K-H-K-G-K-H-K-H-K-H-K-H-K] (SEQ ID NO:3); [K-H-K-H-K-H-K-H-K-G-K-H-K-H-K-H-K-H-K-G-K-H-K-H-K-H-K-H-K] (SEQ ID NO:4); [K-H-K-H-H-K-H-H-K-H-H-K-H-H-K-H-H-K-H-K] (SEQ ID NO:5); [K-K-H-H-H-K-H-H-H-K-K-H-H-H-K-H-H-H-K-K] (SEQ ID NO:6); end-to-end repeats of one or more of the above sequences; the reverse of any of the above sequences; a branched polymer of the formula [K-H-K-H-K-H-K-H-K-G-K-H-K-H-K-H-K-H-K]$_{x+1}$K$_x$ where x is equal to 1 to 30; and a branched polymer of the formula [K-H-K-H-H-K-H-H-K-H-H-K-H-H-K-H-H-K-H-H-K]$_{x+1}$K$_x$ where x is equal to 1 to 30.

In one specific aspect of the invention, the transport polymer comprises a branched polypeptide. In this aspect, the polypeptide is comprised of a backbone peptide and preferably between 1 and 30 peptide branches covalently attached to branching amino acid residues of the backbone peptide. It will be readily appreciated by those of skill in the art that the branching amino acid residues of the peptide backbone may be separated by one or more non-branching amino acid residues. Peptide branches can be joined to branching amino acids by any type of covalent bond, including, but not limited to, polypeptide bonds, ester bonds and disulfide bonds.

Branching amino acid are preferably selected from the group consisting of amino acids with a free amino side chain group, for example, diaminobutyric acid, lysine, arginine, ornithine, diaminopropionic acid and citrulline. Branching amino acids may also be selected from the group consisting of amino acids with a free carboxyl side chain group, for example, glutamic acid, aspartic acid and homocitrulline. The backbone peptide can also be made up of several different branching amino acid residues. Preferably the branching amino acids are lysine.

Peptide branches are preferably independently selected from the group consisting of linear or branched polypeptides (i) at least from about 10 amino acid residues, (ii) comprising from about 5 to 100% histidine residues, (iii) and comprising from 0 to about 95% non-histidine amino acid residues. In a preferred aspect of the invention, the peptide branches of the invention have a formula selected from the group consisting of: [K-H-K-H-K-H-K-G-K-H-K-H-K] (SEQ ID NO:1); [K-H-K-H-K-H-K-G-K-H-K-H-K-H-K] (SEQ ID NO:2); [K-H-K-H-K-H-K-H-K-G-K-H-K-H-K-H-K-H-K] (SEQ ID NO:3); [K-H-K-H-K-H-K-H-K-G-K-H-K-H-K-H-K-H-K-G-K-H-K-H-K-H-K-H-K] (SEQ ID NO:4); [K-H-K-H-H-K-H-H-K-H-H-K-H-H-K-H-H-K] (SEQ ID NO:5); [K-K-H-H-K-H-H-H-K-K-H-H-K-H-H-H-K-K] (SEQ ID NO:6); end-to-end repeats of one or more of the above sequences; the reverse of any of the above sequences; [K-H-K-H-K-H-K-H-K-G-K-H-K-H-K-H-K-H-K]$_{x+1}$K$_x$ where x is equal to 1 to 30, but more preferably 1 to 5; and [K-H-K-H-H-K-H-H-K-H-H-K-H-H-K-H-H-K]$_{x+1}$K$_x$ where x is equal to 1 to 30, but more preferably 1 to 5.

The transport polymer may interact with an intracellular delivery component, such as a liposome, through non-covalent or covalent interactions. For example, where the transport polymer consists only of a linear polypeptide, the transport polymer, by pseudotyping viruses to encode its polypeptide, can become part of the viral coat.

The transport polymer may interact with a pharmaceutical agent through non-covalent or covalent interactions. Alternatively, the transport polymer does not have to interact directly with the pharmaceutical agent, but rather, the pharmaceutical agent interacts with the intracellular delivery component(s), which in turn interact with the transport polymer, in the context of the overall complex.

The transport polymer may also comprise a polypeptide-"synthetic monomer" copolymer. In this embodiment, the transport polymer backbone comprises covalently linked segments of polypeptide and segments of synthetic monomer or synthetic polymer. Preferably, the synthetic monomer or polymer is biocompatible. Preferable synthetic monomers include ethylenically or acetylenically unsaturated monomers containing at least one reactive site for binding to the polypeptide. Suitable monomers as well as methods for preparing a polypeptide-"synthetic monomer" copolymer are described in U.S. Pat. No. 4,511,478, for "Polymerizable compounds and methods for preparing synthetic polymers that integrally contain polypeptides," by Nowinski et al, which is herein incorporated by reference. ps 5.2.2 Intracellular Delivery Component The pharmaceutical agent delivery composition of the invention suitably comprises an intracellular delivery component. The intracellular delivery component can be viral or non-viral component.

Suitable viral intracellular delivery components include retroviruses (e.g., murine leukemia virus, avian, lentivirus), adenoviruses and adeno-associated viruses, herpes simplex viruses, rhinovirus, Sendai virus, and Poxviruses.

Suitable non-viral intracellular delivery components include lipids and various lipid-based substances, such as liposomes and micelles, as well as various polymers known in the art.

Suitable lipids include, for example, phosphoglycerides, sphingolipids, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, dilinoleoylphosphatidylcholine, glycosphingolipid, amphipathic lipids. The lipids may be in the form of unilamellar or multilamellar liposomes.

The intracellular delivery component preferably comprises a cationic lipid. Many such cationic lipids are known in the art. A variety of cationic lipids have been made in which a diacylglycerol or cholesterol hydrophobic moiety is linked to a cationic headgroup by metabolically degradable ester bond, for example: 1,2-Bis(oleoyloxy)-3-(4'-trimethylammonio)propane (DOTAP), 1,2-dioleoyl-3-(4'-trimethylammonio)butanoyl-sn-glycerol (DOTB), 1,2-dioleoyl-3-succinyl-sn-glycerol choline ester (DOSC) and cholesteryl (4'-trimethylammonio)butanoate (ChoTB). Other suitable lipids include cationic, non-pH sensitive lipids, such as: 1,2-dioleoyl-3-dimethyl-hydroxyethyl ammonium bromide (DORI), 1,2-dioleyloxypropyl-3-dimethyl-hydroxyethyl ammonium bromide (DORIE), and 1,2-dimyristyloxypropyl-3-dimethyl-hydroxyethyl ammonium bromide (DMRIE). Other non-pH-sensitive, cationic lipids include: O,O'-didodecyl-N-[p-(2-trimethylammonioethyloxy)benzoyl]-N,N,N-trimethylammonium chloride, Lipospermine, DC-Chol (3 beta [N-(N',N"-dimethylaminoethane)carbonyl]cholesterol), lipopoly(L-lysine), cationic multilamellar liposomes containing N-(alpha-trimethylammonioacetyl)-didodecyl-D-glutamate chloride (TMAG), TransfectACE™ (1:2.5 (w:w) ratio of DDAB which is dimethyl dioctadecylammonium bromide and DOPE) (GIBCO BRL) and lipofectAMINE™ (3:1 (w:w) ratio of DOSPA which is 2,3-dioleyloxy-N-[20([2,5-bis[(3-aminopropyl)amino]-1-oxypentyl]amino)ethyl]-N,N-dimethyl-2,3-bis(9-octadecenyloxy)-1-propanaminium trifluoroacetate and DOPE)(GIBCO BRL). Other suitable lipids are described in U.S. Pat. No. 5,965,434, for "Amphipathic PH sensitive compounds and delivery systems for delivering biologically active compounds," by Wolff et al.

Preferred cationic lipids are those that form liposomes in a physiologically compatible environment. Suitable cationic lipids include, for example, cationic lipids selected from the group consisting of 1,2-dioleythyloxypropyl-3-trimethyl ammonium bromide; 1,2-dimyristyloxypropyl-3-dimethyl-hydroxyethyl ammonium bromide; dimethyldioctadecyl ammonium bromide; 1,2-dioleoyl-3-(trimethylammonium) propane (DOTAP); 3β[N-(N',N'-dimethylaminoethane)carbamoyl]cholesterol (DC-cholesterol); 1,2 dioleolyl-sn-glycero-3-ethylphosphocholine; 1,2 dimyristoly-sn-glycero-3-ethylphosphocholine;[1-(2,3-diol-eyloxy)propyl]-N,N,N-trimethyl-ammonium chloride (DOTMA); 1,3-dioleoyloxy-2-(6carboxyspermyl) propylamide (DOSPER); 2,3-dioleyloxy-N-[2(spermine-carboxyamido)ethyl]-N,N, dimethy-1-propanamoniumtrifluoroacetate (DOSPA); and 1,2-dimyristyloxypropyl-3-dimethyl-hydroxyethyl ammonium bromide (DMRIE).

Cationic lipids may be used with helper lipids such as diloleoylphosphatidylethanolamine (DOPE) or cholesterol to enhance transfection. The molar percentages of these helper lipids in cationic liposomes are between 5 and 50%. In addition, pegylated lipids, which can prolong the in vivo half-life of cationic liposomes, can be present in molar percentages between 0.05 and 0.5%.

5.2.3 Pharmaceutical Agent

The pharmaceutical agent delivery composition of the invention suitably comprises a pharmaceutical agent selected from the group consisting of a protein, a peptide, a nucleic acid, an antisense oligonucleotide, a ribozyme, an RNA-cleaving DNA oligonucleotide, a cancer chemotherapeutic agent, an infectious disease chemotherapeutic agent, a diagnostic agent, and any combination of two or more of the above.

With respect to nucleic acid delivery applications, the pharmaceutical agent suitably comprises a nucleic acid, such as DNA or RNA. The nucleic acid is preferably associated with control elements to express the nucleic acid in the target cell population. The expression vector may include inducible or non-inducible promoters preceding the expressed DNA. Examples of inducible promoters include Tet, ecdysone, or steroid-metallothionine promoters. Examples of constitutive non-inducible promoters include long terminal repeat (LTR), simian viral, phosphoglycerate kinase (PGK), b-actin, or cytomegalovirus (CMV) promoters. Furthermore, the promoters allow general (CMV, PGK) or specific expression (e.g. alpha fetoprotein, tyrosinase) of coding DNA. The viral or plasmid based delivery systems may contain multiple promoters to enhance transfection. Moreover, the vector DNA may include IRES (internal ribosome entry site) between different DNA coding sequences, allowing for the translation of more than one polypeptide from the same transcript. Alternatively, a plasmid or a virus can also express the pharmaceutical agent. Formulation of nucleic acid for expression in gene therapy is described extensively in the literature.

A pharmaceutical agent can interact with a transport polymer and/or an intracellular delivery component by non-covalent or covalent interactions. Where the pharmaceutical agent is not nucleic acid, covalent attachment between the transport polymer and pharmaceutical agent is preferred. Such covalent attachment may be direct, for example through a —COOH group (s) of the polymer with an —NH2 or —OH group of the pharmaceutical agent or the reverse. Alternatively, the pharmaceutical agent may be attached to the transport polymer using a coupling agent, such as di-carboiimide. After the coupling reaction, analysis of the number of pharmaceutical agent molecules attached to polymer can then be determined by NMR and mass spectroscopy. These methodologies are well known to those skilled in the art.

5.2.4 Other Components of the Pharmaceutical Agent Delivery Composition

The pharmaceutical agent delivery composition may include further components to enhance transfection to preserve reagents, or to enhance stability of the delivery complex. For example, stabilizing compounds such as polyethylene glycol can be covalently attached to either the lipids or to the transport polymer.

The pharmaceutical agent delivery composition may include a suitable buffer solution whose pH is between 4 and 7.4. Preferably within two hours of neutralizing acidic solutions to between 5.0 and 7.4, the pharmaceutical agent delivery composition is administered. The various components of the pharmaceutical agent delivery composition lyophilized and reconstituted with a buffer between pH 5.0 and 7.4 for use. Stability and solubility of the polymer, particularly when complexed to large negatively charged macromolecules such as DNA, is maintained at slightly acidic solutions.

The pharmaceutical agent delivery composition of the invention may include a dendrimer. The intracellular delivery component and the pharmaceutical agent may together comprise a dendrimer-pharmaceutical agent complex. For instance, a dendrimer and nucleic acid may together comprise a dendrimer-DNA complex.

The pharmaceutical agent delivery composition also suitably includes various delivery-enhancing components known in the art. For example, the composition may include compounds known to enter the nucleus or ligands subject to receptor-mediated endocytosis, and the like. For example, the ligand may comprise a fusogenic viral peptide to disrupt endosomes, allowing the nucleic acid to avoid lysosomal degradation. Other examples of delivery-enhancing components include nuclear proteins, adenoviral particles, transferrin, surfactant-B, anti-thrombomodulin, intercalating agents, hemagglutinin, asialglycoprotein, chloroquine, colchicine, integrin ligands, LDL receptor ligands, and viral proteins to maintain expression (e.g. integrase, LTR elements, rep proteins, oriP and EBNA-1 proteins) or viral components that interact with the cell surface proteins (e.g. ICAM, HA-1, MLV's gp70-phosphate transporter, and HIV's gp120-CD4). Delivery enhancing components can be covalently or non-covalently associated with the transport polymer, the intracellular delivery component, or the pharmaceutical agent. For instance, delivery to a tumor vasculature can be targeted by covalently attaching a -RGD- or -NGR- motif (34,35). This could be accomplished using a peptide synthesizer or by coupling to amino groups or carboxyl groups on the transport polymer with a water-soluble di-carbodiimide (e.g., 1-ethyl-3-(3-dimethyaminopropyl)carboiimide). Both of these methods are known to those familiar with the art.

The pharmaceutical agent delivery composition also suitably comprises a transition metal ion, such as a zinc ion. As shown in the example, the presence of transition metal in the complexes can enhance transfection efficiency.

5.3 Methods for Making Transport Polymers

Polypeptides of the invention can be chemically synthesized and purified by techniques well know in the art:

Polypeptides can be synthesized by employing the N-α-9-fluorenylmethyloxycarbonyl or Fmoc solid phase polypeptide synthesis chemistry using a Rainin Symphony Multiplex Polypeptide Synthesizer.

The standard cycle used for coupling of an amino acid to the polypeptide-resin growing chain generally includes: (1) washing the polypeptide-resin three times for 30 seconds with N,N-dimethylformamide (DMF); (2) removing the Fmoc protective group on the amino terminus by deprotection with 20% piperidine in DMF by two washes for 15 minutes each, during which process mixing is effected by bubbling nitrogen through the reaction vessel for one second every 10 seconds to prevent polypeptide-resin settling, (3) washing the polypeptide-resin three times for 30 seconds with DMF; (4) coupling the amino acid to the polypeptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the polypeptide-resin three times for 30 seconds of DMF. This cycle can be repeated as necessary with the appropriate amino acids in sequence to produce the desired polypeptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in polypeptide synthesis, the resin can be allowed to swell for more efficient coupling by increasing the time of mixing in the initial DMF washes to three 15 minute washes rather than three 30 second washes.

After polypeptide synthesis, the polypeptide can be cleaved from the resin as follows: (1) washing the polypeptide-resin three times for 30 seconds with DMF; (2) removing the Fmoc protective group on the amino terminus by washing two times for 15 minutes in 20% piperidine in DMF; (3) washing the polypeptide-resin three times for 30 seconds with DMF; and (4) mixing a cleavage cocktail consisting of 95% trifluoroacetic acid (TFA), 2.4% water, 2.4% phenol, and 0.2% triisopropysilane with the polypeptide-resin for two hours, then filtering the polypeptide in the cleavage cocktail away from the resin, and precipitating the polypeptide out of solution by addition of two volumes of ethyl ether. Specifically, to isolate the polypeptide, the ether-polypeptide solution can be allowed to sit at −20° C. for 20 minutes, then centrifuged at 6,000×G for 5 minutes to pellet the polypeptide, and the polypeptide can be washed three times with ethyl ether to remove residual cleavage cocktail ingredients. The final polypeptide product can be purified by reversed phase high pressure liquid chromatography (RP-BPLC) with the primary solvent consisting of 0.1% TFA and the eluting buffer consisting of 80% acetonitrile and 0.1% TFA. The purified polypeptide can then be lyophilized to a powder.

The invention also provides a transport polymer comprising a branched polypeptide. Branched versions of the transport polymer of the present invention are made by including one or more amino acids within the amino acid sequence with a free side chain capable of forming a polypeptide bond with one or more amino acids (and thus capable of forming a "branch"), and reacting a side chain to that locus.

Branched polypeptides may be prepared by any method known in the art for covalently linking any naturally occurring or synthetic amino acid to any naturally occurring or synthetic amino acid in a polypeptide chain which has a side chain group able to react with the amino or carboxyl group on the amino acids so as to become covalently attached to the polypeptide chain. In particular, amino acids with a free ammo side chain group, such as, but not limited to, diaminobutyric acid, lysine, arginine, ornithine, diaminopropionic acid and citrulline, can be incorporated into a polypeptide so that an amino acid can form a branch therewith, for example, by forming a polypeptide bond to the free amino side group, from that residue. Alternatively, amino acids with a free carboxyl side chain group, such as, but not limited to, glutamic acid, aspartic acid and homocitrulline, can be incorporated into the polypeptide so that an amino acid can form a branch therewith, for example, by forming a polypeptide bond to the free carboxyl side group, from that residue. The amino acid forming the branch can be linked to a side chain group of an amino acid in the polypeptide chain by any type of covalent bond, including, but not limited to, polypeptide bonds, ester bonds and disulfide bonds.

For example, but not by way of limitation, branched polypeptides can be prepared as follows: (1) the amino acid to be branched from the main polypeptide chain can be prepared as an N-α-tert-butyloxycarbonyl (Boc) protected amino acid pentafluorophenyl (Opfp) ester and the residue within the main chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the polypeptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12 N HCl; (4) the solution containing the polypeptide can be dehydrated by adding 2–5 grams magnesium sulfate, filtering out the magnesium sulfate, and evaporating the remaining solution to a volume of about 2–5 ml; (5) the dipolypeptide can then be precipitated by addition of ethyl acetate and then 2 volumes of hexanes and then collected by filtration and washed two times with cold hexanes; and (6) the resulting filtrate can be lyophilized to achieve a light powder form of the desired dipolypeptide. Branched polypeptides prepared by this method will have a substitution of diaminobutyric acid at the amino acid position which is branched. Branched polypeptides containing an amino acid or amino acid analog substitution other than diaminobutyric acid can be prepared analogously to the procedure described above, using the N-F-moc coupled form of the amino acid or amino acid analog.

Polypeptides of the transport polymer can also be encoded by vial DNA and be expressed on the virus surface. Alternatively, histidine could be covalently linked to proteins through amide bonds with a water soluble di-carboimide.

5.4 Methods of Using Pharmaceutical Agent Delivery Compositions

The invention comprises a method for delivering a pharmaceutical agent to the interior of a cell, said method comprising contacting the cell with a pharmaceutical agent delivery composition of the invention. Preferably, the compositions are administered to animals, including humans, by injection. Injection may be systemic (by i.v.) or local (for example, to the site of a tumor).

In general, a cell to be treated may include any animal, plant or bacterial cell that is susceptible to intracellular delivery of a pharmaceutical agent using the delivery composition either in vivo or in vitro. For example, suitable cellular targets include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megalaryocytes, granulocytes; various stem or progenitor cells, in particular hematopoietic stem or progenitor cells, e.g., as obtained from bone marrow, umbilical cord blood, peripheral blood, fetal liver, and the like. In one aspect, the cell is selected from the group consisting of lung cells, liver cells, endothelial cells, muscle cells, skin cells, hematopoietic stem cells and tumor cells.

Examples of genetic and/or non-neoplastic diseases potentially treatable with the compositions and methods includes: adenosine deaminase deficiency; purine nucleoside phosphorylase deficiency; chronic granulomatous disease with defective p47phox; sickle cell with HbS, β-thalassemia due to inadequate production of β hemoglobin; Faconi's anemia; familial hypercholesterolemia due to a defective low -density lipoprotein receptor, α1-antitrypsin deficiency; phenylketonuria due to phenylalanine hydroxylase deficiency; ornithine transcarbamylase deficiency; apolipoprotein E deficiency; hemophilia A and B due to factor VIII and IX deficiency, respectively; muscular dystrophy due to dystrophin, laminin-2, or sacroglycans mutations; cystic fibrosis due to CFTR mutations; Parkinson due to tyrosine hydroxylase deficiency, retinitis pigmentosa, lysosomal storage disease (i.e., mucopolysaccharide type 1, Hunter, Hurler and Gaucher), diabetic retinopathy, human immunodeficiency virus disease virus infection, acquired anemia, cardiac and peripheral vascular disease, and arthritis. In these diseases, the therapeutic gene may encode a replacement enzyme or protein of the genetic or acquired disease, an antisense or ribozyme molecule, a decoy molecule, or a suicide gene product.

Ex vivo and in vivo gene therapy with therapeutic DNA could also be used in cancer. Gene therapy applications toward cancer include the following: 1) enhanced immunogeniticy of tumor (e.g., insert foreign antigens, cytokines, ICAMI, MHC class II and/or B7 co-stimulatory molecule genes); 2) genetically alter immune cells to increase function (e.g., cytokines, co-stimulatory molecules, and a tumor-specific T cell receptor; 3) insert suicide gene into a tumor (e.g., thymidine kinase, cytosine deaminase genes); 4) block oncogene expression (e.g. antisense K-ras, intracellular antibodies); 5) insertion of a tumor suppressor gene (e.g., p53, rb, p21, or p16 genes); 6) antiangiogenic gene therapy (e.g. angiogstatin, endostatin, antithrombin III, KDR, or antisense to VEGF or PDECGF genes); 7) protect tissues from the systemic toxicities of chemotherapy (e.g., multiple drug resistance type I, DNA repair enzymes, alkyltranferase, dihydrofolate reductase genes); 8) induce normal tissues to produce antitumor substances, production of recombinant vaccines for the prevention and treatment of malignancy (e.g., interferon gene); 9) local radioprotection of normal bystander tissues with antioxidant overexpression (e.g., glutathione synthetase or transferase, manganese superoxide dismutase genes; 10) insertion of genes to enhance tumor sensitivity to radiation (e.g., manganse superoxide dismutase, TNF-α); 11) transfer of genes that block expression of receptors critical for tumor cell survival (e.g., EGF, IGF-1 receptor genes); 12) transfer of genes necessary for survival (e.g., Fas or Fas ligand genes); 13) transfer of antimetastatic disease (e.g., nitric oxide synthetase); and 14)production of recombinant vaccines for the prevention and treatment of malignancy (e.g., injection of CEA, BCG, MAGE-1, tyrosinase, muc-1, Mum-1 genes).

The present invention also provides a method of ex vivo gene therapy comprising: (i) removing a cell from a subject; (ii) delivering a nucleic acid to the interior of the cell by contacting the cell with a pharmaceutical agent delivery composition of the present invention; and (iii) administering the cell to the subject In one aspect, the cell is selected from the group consisting of lung cells, liver cells, endothelial cells, muscle cells, skin cells and hematopoietic stem cells.

The resulting recombinant cells can be delivered to a subject by various methods known in the art. In a preferred embodiment, the recombinant cells are injected, e.g., subcutaneously. In another embodiment, recombinant skin cells may be applied as a skin graft onto the patient Recombinant blood cells (e.g., hematopoietic stem or progenitor cells) are preferably administered intravenously. The cells can also be encapsulated in a suitable vehicle and then implanted in the subject (see, e.g., Dionne et al. PCT Publication WO 92/19195, dated Nov. 12, 1992). The amount of cells administered depends on a variety of factors known in the art, for example, the desired effect, subject state, rate of expression of the chimeric polypeptides, etc., and can readily be determined by one skilled in the art.

6. EXAMPLES

The transport polymer of the Examples is based on a lysine and histidine copolymer. Lysine is known to complex with and partially neutralize the negative charge of plasmid DNA. The data-presented herein is consistent with the idea that the histidine component of the copolymer buffers and aids in the release of plasmid DNA from the pre-lysosomal vesicles, and is further consistent with the idea that the cationic liposomes neutralize the remainder of the DNA charge and provide a scaffold for the polymer: DNA complex.

6.1 Materials

Cells: A breast cancer cell line, MDA-MB-435, Bovine Aortic Endothelial Cells (BAEC), Chinese Hamster Ovary (CHO) and NIH-3T3 cells were maintained in DMEM containing 10% fetal calf serum and 20 mM glutamine.

Transport Polymers: The biopolymer core facility at the University of Maryland synthesized the polymers on a Ranim Voyager synthesizer (PTI, Tuscon, Ariz.). The polymers were then purified on an HPLC (Beckman, Fullerton, Calif.) and analyzed with mass spectroscopy (Perseptive Biosystems, Foster City, Calif.) to verity the predicted molecular mass. A glycine inserted after every ninth amino acid increased the yield and quality of histidine copolymers composed of 19 or more amino acids.

Measurement of the S-K and histidine copolymers with poly-L-lysine (Sigma Co., St Louis, Mo.) used as a standard were done with 2,6-dinitro4-trifluoromethylbenzene-sulfonate (Pierce Co., Rockford, Ill.) as previously described (32,33). The following polymers were made: 1) H-K (13mer) [K-H-K-H-K-H-K-G-K-H-K-H-K] (SEQ ID NO:1); 2) H-K (19mer) [K-H-K-H-K-H-K-H-K-G-K-H-K-H-K-H-K-H-K] (SEQ ID NO:3); 3) H-K (29 mer) [K-H-K-H-K-H-K-H-K-G-K-H-K-H-K-H-K-H-K-G-K-H-K-H-K-H-K-H-K] (SEQ ID NO:4); 4) HH-K (20mer) [K-H-K-H-H-K-H-H-K-H-H-K-H-H-K-H-H-K-H-K] (SEQ ID NO:5); 5) HHH-K (20mer) [K-K-H-H-H-K-H-H-H-K-K-H-H-H-K-H-H-H-K-K] (SEQ ID NO:6); 6) Y-HK [Y G-R-K-K-R-R-Q-R-R-R-G-K-H-K-H-K-H-K-H-K-H-K-H-K-H-K-H-K] (SEQ ID NO:7); 7) Y-HH [Y-G-R-K-K-R-R-Q-R-R-R-H-H-K-H-H-K-H-H-K-H-H-K-H-H-K] (SEQ ID NO:8); 8) K-HK [K-K-H-K-H-K-H-K-H-K-G-K-H-K-H-K-H-K-K] (SEQ ID NO:9); 9) S-K (19 mer) [K-S-K-S-K-S-K-S-K-G-K-S-K-S-K-S-K-S-K] (SEQ ID NO:10); 10) H-S (19 mer) [S-H-S-H-S-H-S-H-S-G-S-H-S-H-S-H-S-H-S] (SEQ ID NO: 11); 11) poly-L-lysine (19mer) [K-K-K-K-K-K-K-

K-K-G-K-K-K-K-K-K-K-K] (SEQ ID NO: 12); 12) H-K2b [K-H-K-H-K-H-K-H-K-G-K-H-K-H-K-H-K-H-k]$_2$K; 13) H-K3b [K-H-K-H-K-H-K-H-K-G-K-H-K-H-K-H-K-H-K]$_3$ K$_2$; 14) H-K4b [K-H-K-H-K-H-K-H-K-G-K-H-K-H-K-H-K-H-K]$_4$K$_3$; 15) HH-K2b [K-H-K-H-H-K-H-H-K-H H-K-H-H-K-H-H-K-H-H-K]$_2$K; 16) HH-K3b [K-H-K-H-H-K-H-H-K-H-H-K-H-H-K-H-H-K-H-H-K]$_3$K$_2$; and 17) HH-K4b [K-H-K-H-H-K-H-H-K-H-H-K-H-H-K-H-H-K-H-H-K-H]$_4$K$_3$. Note that 12) through 17) are branched polymers in which either an H-K (19-mer) or an HHK (20-mer) polymer is attached to the α and ε amino groups of a lysine residue and the central core of lysines are linked to one another by peptide bonds (FIG. 16).

Preparation of Liposomes: Preparation of liposome:plasmid complexes have been previously described (8, 30). In brief, DH5α bacteria (Life Technologies, Gaithersburg, Md.) containing plasmids were grown in Superbroth to mid-log phase. The plasmids were then purified with Qiagen columns. An analytical gel of each plasmid (cut and uncut) was done to ensure that there was no contamination with other nucleic acids. Liposomes were composed of 1,2-dioleoyl-3-trimethylammonium-propane (DOTAP) (Avanti, Birmingham, Ala.). After hydration of the lipids, the liposomes were sonicated until clear with a Branson 1210 bath sonicator in the presence of argon. The liposomes were then extruded through 50 nm polycarbonate membranes with LipsoFast- Basic (Avestin Inc., Ottawa, ON). The liposomes final concentration was 1 μg/μl.

6.2 In Vitro and In Vivo Transfection Studies:

$4.5 \times 10^4$ cells (MDA-MB435, NIH3T3 or CHO) were initially plated into 24 well dishes. After 48 hours, when the cells were 60 and 80% confluent, cells were transfected with a plasmid encoding luciferase (PCI-Luc). In transfection experiments, the copolymer was initially incubated with PCI-Luc for 30 minutes in OptiM. The amount of copolymer which varied from 0.25 nmole to 15 nmole was mixed with the plasmid or oligonucleotide. The concentration of DNA varied from 0.25 μg to 0.75 μg. No visible aggregation of the polymer with the plasmid DNA was apparent at these concentrations. Cationic liposomes were then added, gently mixed, and then allowed to stand for an additional 30 minutes. The polymer:liposome:DNA complex was then diluted with either OptiM or OptiM+10% serum. In experiments utilizing lysomotropic agents, either chloroquine (Sigma, St. Louis, Mo.) or bafilomycin A$_1$ (Sigma) was added to the media at concentrations of 10 ng/ml and 25 μM, respectively. Four hours after transfection, the complexes were removed and DMEM with 10% serum was added. Forty-eight hours later, luciferase levels were measured with the Turner 20/20 luminometer. Duplicates were done for each concentration and each experiment was performed twice.

For in vivo studies, $3.0 \times 10^5$ MDA-MB435 cells were injected bilaterally into the mammary fat pad of six nude rice. After palpable tumors were present, the transfection complexes were injected into the tumors. The liposome-PCI-Luc complex was injected into one tumor and the polymer:liposome:PCI-Luc complex was injected into the contalateral tumor. As with the in vitro experiments, the polymer was first mixed with the DNA before adding the cationic liposomes. More specifically, 264 nmol of the linear H-K polymer was mixed with 28 μg of DNA. The volume for this reaction was 150 μl. After 1 hour, 150 additional microliters of a solution containing 504 nmol of a cationic liposomal solution was added to the polymer and DNA complex After one hour of incubation, the solution was partially neutralized to a pH 6.5 or neutralized to 7.4. Within 30 minutes to 2 hours after neutralization, each tumor was injected with a 25 μl of solution containing 42 nmole of liposomes, 22 nmole of the linear histidine copolymer, and 2.34 μg of DNA. The control tumors received a similar dosage of liposomes and DNA complexes. Twenty-four hours after injection, the tumors were excised and placed in 500 μl of reporter lysis buffer (Promega, Madison, Wis.). The samples were then homogenized for 30 seconds followed by one freeze thaw cycle. After the samples were centrifuged, luciferase activity was measured in the supernatant.

At higher concentrations of liposomes, polymer, and DNA such as those utilized in the above in vivo experiments, maintaining the solution between pH-4.0 and 5.5 prevented precipitation during the reaction phase. Thirty minutes to two hours prior to injection of complexes, the solution was neutralized to between pH 5.0 and 7.4. When higher concentrations of polymer and DNA as used with in vivo experiments were injected without liposomes, the final pH of the injectable solution is preferably between 5.0 and 6.5 to prevent precipitation.

6.3 Affinity Determinations

Liposomes were prepared as described above except that the liposomes also contained fluorescent lipid and bitotinylated lipids. The ratio of DOTAP: 1,2-dioleoyl-sn-glycero-3-phosphoethanolamine-n-(7-nitro2-1,3-benzoxadiazol-4-yl):1,2-dioleoyl-sn-glycero-3-phosphoethanolamine-n- (cap biotinyl) was 97.5:2.0:0.5. Labeled histidine copolymer was prepared by reacting iodo[-1-$^{14}$C]acetamide (50 mCi/mole) in NaPhos buffer pH 7.4 overnight. An average of one in 20 histidines were modified and the labeled histidine copolymer was separated from the iodoacetamide on a G-15 Sephadex column chromatography. PCI-Luc was nick translated with deoxycytidine 5'-[α-$^{32}$P] triphosphate (3000 Ci/mmole).

The polymer-liposome:DNA and the liposome:DNA complexes were prepared as described above except that labeled DNA and/or polymer was added. After the complexes were prepared, an equal volume (150 μl) of DMEM or DMEM with serum was added to the complexes for one hour. The complexes were then mixed with 10 μl of streptavidin dynabeads solution for 30 minutes and then washed three times with 200 μl of a 1 M NaCl, 10 mM Tris, and 1 mM EDTA solution. The counts attached to the streptavidin beads were then counted with the Beckman scintillation counter. Quantitation of liposomes was determined with the fluorescent multiwell reader, CytoFluor 2350 (Millipore).

6.4 Results on the Transfection Efficiency of a Polymer: Liposome:DNA Complex 6.4.1 Effect of H-K Copolymers on Transfection Efficiency of a Liposome:DNA Complex.

To investigate the effect of the copolymer His-Lys (H-K) on transfection efficiency of a liposome:DNA complex, several different combinations of concentrations of H-K (19-mer) (SEQ ID NO:3), DNA and liposomes were examined. The putative copolymer: liposome: DNA complex was incubated with MDA-MB435 breast cancer cells for 4 hours in the absence of serum. Over a wide range of concentrations, the histidine copolymer enhanced the transfection efficiency of a liposome: PCI- luciferase (Luc) complex (FIG. 1). The addition of the histidine copolymer increased transfection efficiency of the liposome: PCI-Luc complex up to 10-fold compared to the liposome: PCI-Luc complex. The histidine copolymer increased transfection efficiency of the liposome: PCI-Luc complex at all concentrations with an optimal amount in this system, shown at 7.5 nmole. No morphologic evidence of cellular toxicity due to the polymer was seen even at concentrations of 0.5 mM. This enhancement of transfection efficiency by the histidine copolymer was not limited to MDA-MB435 cells. The histidine copolymer increased transfection efficiency of liposome: DNA complexes in CHO ($p<0.0001$) and NIH-3T3 ($p<0.0185$) cells as well (FIG. 2). The combination of a linear H-K polymer and liposome carriers was synergistic in their enhancement of transfection efficiency. Besides liposomes, we determined that the H-K polymer enhanced the transfection efficiency of delivery systems such as the Superfect (Qiagen) dendrimer (data not shown).

6.4.2 Effect of Varying the Length of the Histidine Copolymer on Transfection Efficiency.

The effects of varying the length of the histidine copolymer on transfection efficiency was examined by comparing an H-K (13 mer) (SEQ ID NO:1), an H-K (19 mer) (SEQ ID NO:3), and an H-K (29 mer) (SEQ ID NO:4) of the histidine copolymer. While all three polymers increased the transfection efficiency of the liposome: PCI-Luc complex ($p<0.05$) in MDA-MB435 cells, the 19 and 29-length polymers increased transfection efficiency more than the 13 mer ($p<0.05$) (FIG. 3). Although the 19 mer was not statistically superior to the 29 mer with regards to enhancing transfection efficiency, the 19 mer of H-K appeared to be somewhat better than the 29 mer at most concentrations of liposomes and DNA.

6.43 Effect of Polymer Branching on Transfection Efficiency of a Polymer:Liposome:DNA Complex.

Increased branching of the histidine copolymer can be significantly more effective at enhancing transfection efficiency than the linear co-polymer. In a comparison of transport polymers consisting of a linear (H-K (19mer) (SEQ ID NO:3)) or a branched (H-K2b, H-K3b or H-K4b) polypeptide, in the absence of serum, the dosage of the transport polymer used decreased by 20-fold and the transfection efficiency increased as compared to the linear H-K polymer by approximately 10-fold (FIG. 4).

6.4.4 Effect of Serum on Transfection Efficiency.

Since serum is know to frequently reduce the transfection efficiency of liposomes in vitro and in vivo, we examined the effect that media containing serum had on the histidine copolymer: liposome: DNA complexes. In the presence of serum, a linear histidine copolymer when added to the liposome: plasmid DNA complex had a 100-fold greater transfection efficiency than the liposome:PCI-Luc complexes alone ($p<0.002$) (FIG. 5). Furthermore, in contrast to liposome: PCI-Luc complexes, the transfection efficiency of the H-K: liposome: PCI-Luc: complexes was similar in the presence or absence of serum. In contrast to the H-K polymer, poly-L-lysine in combination with liposomes was not resistant to serum and the transfection efficiency with the polylysine:liposome carrier was markedly decreased in the presence of serum.

In a separate experiment, it was investigated whether the histidine copolymer increased DNA binding to liposomes. H-K polymer: liposome: DNA (PCI-Luc) and liposome: DNA complexes were prepared as in the transfection experiments. An equal volume of media with or without serum (10%) was then added to these complexes for one hour. Streptavidin beads were then added to the complexes with intermittent mixing for 30 minutes. After washings, the amount of DNA complexed to liposomes was quantitated. Overall, histidine copolymer increased DNA binding to liposomes from 1.5 to 3-fold (over liposomes alone) in the presence or absence of serum FIG. 6).

6.4.5 Effects on Transfection Efficiency After Varying the Order of Addition of Histidine Copolymer, Liposome, and DNA.

In order to determine whether the histidine copolymer is physically linked to the liposome: DNA complex, the effect on transfection efficiency was examined after varying the order of addition of these three components. When the polymer was first incubated with the DNA, and then mixed with the liposomes, the greatest enhancement of transfection efficiency ($p<0.05$) (FIG. 7). With all other mixing permutations, the transfection efficiency with H-K was reduced. Lesser transfection efficiency occurred when liposomes were first incubated with plasmid DNA, and later the polymer was added. Intermediate reductions in transfection occurred when the liposomes and polymer were simultaneously added to plasmid DNA. Similar results occurred with or without serum. Unless the polymer is first mixed with the DNA, the low molecular weight polymer may not be able to compete adequately with the cationic liposomes for the negatively charged plasmid DNA. Although enhancement of transfection efficiency has been reported to occur as a result of interaction of cationic polymers with inhibitory proteins in the serum (9), pre-mixing the histidine copolymer with serum did not enhance the transfection efficiency of the liposome: DNA complex (data not shown). These findings suggest that the polymer is integrated into the liposome: DNA complex, and this tripartite complex is important for increased transfection efficiency.

6.4.6 Effect of Histidine on the Transfection Efficiency of the Transport Polymer Since histidine is the distinctive component of the transport polymer, the role that histidine plays in augmenting the transfection efficiency of the polymer was examined. To investigate whether histidine enhances transfection efficiency, serine was substituted for histidine while maintaining the same number of lysines in this copolymer. In the absence of serum, the S-K (19-mer) (SEQ ID NO:10) polymer enhanced the transfection efficiency slightly more than when no polymer was added. However, when compared to the H-K (19-mer) (SEQ ID NO:3), the S-K (19-mer) (SEQ ID NO:10) copolymer was significantly less effective at increasing the transfection efficiency (FIG. 8). Thus, the histidine moiety of the polymer plays a significant role in increasing the transfection efficiency. Since the histidine component of the histidine copolymer is important in augmenting transfection efficiency of the polymer, other amino acids may be substituted for lysine in the copolymer. An arginine-histidine copolymer, H-R (19-mer) (SEQ ID NO: 13), is significantly better than H-K at enhancing transfection efficiency (FIG. 9).

6.4.7 Effect of Lysosomotropic Agents on Transfection Efficiency.

Since H-K is markedly more effective than the S-K copolymer, the buffering capacity of histidine may have a role in augmenting the transfection efficiency of the histidine copolymer. To determine if the buffering component of the histidine copolymer increases transfection efficiency, the effects of various lysosomotropic agents (chloroquine, bafilomycin $A_1$) on the uptake of the liposome: DNA complex were examined. Surprisingly, incubation with bafilomycin $A_1$ or chloroquine significantly increased the transfection of the H-K: liposome: PCI-Luc triplex in NIH-3T3 and CHO cells. The enhancement with bafilomycin $A_1$ was particularly string and increased the transfection efficiency of the triplex by 5-fold ($p<0.002$) FIG. 10). In contrast, bafilomycin $A_1$ did not enhance the transfection efficiency of the liposome: PCI-Luc complex in the absence of the histidine copolymer. It thus appears likely that synergism occurs between the H-K component of the triplex and bafilomycin $A_1$ to increase transfection efficiency. Recently, another lysosomotropic agent, chloroquine, was reported to enhance the transfection efficiency of low molecular weight PEI, a polymer that also buffers pre-lysosomal vesicles (20). Transfection synergy between the low molecular weight PEI and chloroquine was thought to be due to partial buffering of the pre-lysosomal vesicles by PEI. In contrast, chloroquine did not increase the transfection efficiency of a large molecular weight PEI carrier, which more effectively buffers the pre-lysosomal vesicles. Thus, it appears that the H-K polymer acts, at least in part, by buffering the pH of the pre-lysosomal vesicles in Chinese hamster ovary cells. Nevertheless, it is important to note that lysosmotropic agents did not increase transfection efficiency of the H-K polymer liposome: DNA complex in MDA-MB435 cells and only minimally increased transfection efficiency in NIH3T-3 cells.

6.4.8 In vivo Transfection Study.

Since the histidine copolymer enhanced in vitro transfection efficiency, the effect of the histidine copolymer in vivo was investigated. A significant limitation of non-viral carriers has been their low transfection efficiency in vivo. When human breast cancer cells, which had been implanted into the mammary fat pad of nude mice, grew to palpable tumors, either the H-K: liposome: PCI-Luc or liposome: PCI-Luc complexes were injected into the tumors and expression of the reporter gene was compared. A 15-fold enhancement of luciferase activity was observed in tumors injected with H-K: liposome: PCI-Luc compared to liposome: PCI-Luc ($p<0.02$) (FIG. 11). Previously, liposomes were used as carriers of anti-angiogenic genes to inhibit tumor growth (31). The expression of these transfected secreted antiangiogenic proteins was quite low resulting in moderate reduction of tumor size. The H-K: liposome carrier should augment the secretion and antitumor efficacy of these proteins. Furthermore, the histidine copolymer or a derivative may have widespread applications in other gene therapies.

6.4.9 Comparison of H-K polymer and Poly-L-lysine

H-K was also compared to poly-L-lysine (19-mer) (SEQ ID NO:12). Poly-L-lysine (PLL) is known to enhance the transfection efficiency of liposome:DNA complexes. The PLL used has the same number of amino acids as the H-K (19-mer) polymer used for comparison, and its amino acid makeup is K-K-K-K-K-K-K-K-K-G-K-K-K-K-K-K-K-K-K (SEQ ID NO:12). The data (see FIG. 12) demonstrates that even though PLL has twice as many lysines as H-K, H-K is about 50 times more effective than PLL in the presence of serum. Since serum is thought to reduce transfection efficiency by stripping away the DNA from the carriers (liposomes and polymer), it was surprising that poly-L-lysine polymer with twice as many lysines to bind the DNA compared to H-K was a significantly less effective transfection agent than H-K in the presence of serum.

6.4.10 Effect of the Histidine Order on Transfection Efficiency.

The sequence order of the H-K amino acids can affect transfection efficiency. Polymers H-K, Y-HK (SEQ ID NO:7), and Y-HH (SEQ ID NO:8) were mixed initially with DNA and then liposomes were added as previously described. While all accelerated useful transfection efficiency, the Y-HH polymer significantly enhanced the uptake of liposomes in the presence or absence of serum (FIG. 13).

Since the Y peptide component (Y-G-R-K-K-R-R-Q-R-R-R) (SEQ ID NO: 17) was present in both the Y-HK and the Y-HH polymers, the critical sequence that enhanced uptake in the Y-HH polymer was the HH component (H-H-K-H-H-K-H-H-K-H-H-K-H-H-K) (SEQ ID NO: 15). For this reason, the latter sequence is a currently preferred embodiment of the invention.

To further investigate the extent to which histidine order could affect transfection efficiency, four polymer solutions containing a different linear histidine copolymer (H-K (19-mer) (SEQ ID NO:3), HHH-K (20-mer) (SEQ ID NO:6), HH-K (20-mer) (SEQ ID NO:5), or K-HK (21-mer) (SEQ ID NO:9)) were mixed in amounts ranging from 0.125 µl to 2.5 µl with 0.75 µg DNA. The concentration of each of the polymer solutions was 15 µg/µl. After 30 minutes, 1.5 µg of liposomes were added. After adding the delivery compositions to endothelial cells (BAEC) for 4 hours, the cells were washed, and luciferase activity measured 48 hours later (FIG. 14). The results suggest that both histidine order and polymer concentration affect transfection efficiency.

6.4.11 Effect of Adding Transition Metals on Transfection Efficiency.

To determine the effect of adding transition metals on the transfection efficiency of a polymer:DNA complex, 0.25 µg H-K2b, 0.125 µg H-K3b, or 0.125 µg H-K4b were initially mixed with 0.75 µg DNA. After 30 minutes, cationic liposomes were added for 30 minutes. $Zn^{2+}$ was then added in an amount ranging from 0 to 2.00 µg/ml. As a control, various amounts of zinc were added to the liposome:DNA complex. The addition of zinc can enhance transfection efficiency of polymer:liposome:DNA complexes (FIG. 15).

6.4.12 Comparison of H-K2b:Liposome Carriers with PEI.

Polyethylenimine (PEI) is a commonly used cationic polymer utilized in non-viral gene delivery transfer systems. To compare PEI with the H-K2b:liposome carrier, 0.5 µg of PEI was first mixed with 0.75 µg of DNA for 1 hour. H-K2b (025 µg) was mixed initially with DNA (0.75 µg) for 30 minutes followed by the addition of cationic liposomes (1.5 µg). These two complexes were then compared for their ability to transfect MDA-MB435 cells m the presence or absence of serum. Forty-eight hours after transfection, luciferase activity was determined. In the presence or absence of serum, the transfection system comprising the transport polymer of the present invention was more than 10-fold better than PEI in transporting DNA into MDA435 cells ($p<0.01$, H-K4b/liposome vs. PEI) (FIG. 16). This illustrates that the combination of H-K2b and liposomes significantly improves transfection compared to PEI, one of the most effective cationic polymers currently used.

6.4.13 Effect of Polymer Branching in the Absence of Liposomes

Effect on transfection efficiency of a polymer:DNA complex: To determine the effect of branching on the transfection efficiency of a polymer:DNA complex, 7.5 nmol of H-K or 0.375 nmol of HH-K4b was mixed with PCI-Luc, and luciferase activity was measured as described above. The branched HH-K4b polymer showed better ($p<0.05$) transfection efficiency over the linear H-K polymer (FIG. 18a). HH-K4b as a sole carrier of DNA was also better at enhancing luciferase expression than H-K3b, HH-K2b, and H-K4b (data not shown).

Effect on uptake of a polymer:oligonucleotide complex: In a second experiment, the same amount of HK or HHK4b was mixed with 0.75 µg of a 5'-end fluorescein-labeled randomly generated oligonucleotide(32-mer) for 30 minutes. This complex was added to the MDA-MB435 cells for 4 hour incubation. Twenty-four hours later, the cells were then washed, and measured by CytoFluor fluorescence Measurement System (Millipore, Bedford, Mass.). The branched HH-K4b polymer significantly enhanced uptake (p<0.05, Mann-Whitney Rank-Sum Test) of oligonucleotides when compared to a linear HK polymer: oligonucleotides complex FIG. 18b).

These results demonstrate that a branched histidine copolymer increases transfection efficiency of plasmids and uptake of oligonucleotides even in the absence of an intracellular delivery component.

In vivo delivery of pharmaceutical agents. The following example demonstrates that HH-K4b has utility in vivo as a carrier of low molecular weight DNA molecules in the absence of an intracellular delivery compound. In this example, the receptor of VEGF mRNA with a DNA oligonucleotide that has enzymatic activity (also called DNAzyme) (36) was targeted. The VEGF receptor is essential for tumor angiogenesis and consequently tumor growth. After breast cancer cells (MDA-MB-435 cells) were injected into nude mice and the tumors grew to a visible size, the tumor was injected with the therapeutic polymer-DNA complex. The tumor was injected every 5 days for a total of 5 injections. There were 4 treatment groups: 1) untreated, 2) HH-K4B carrier alone, 3) HH-K4b+DNAzyme, and 4) HH-K4b +antisense oligonucleotides. To prepare the complex for injection, 45 µg of the HH-K4b polymer diluted in 150 µl of water was mixed with 24 µg of oligonucleotide, also diluted in 150 µl of water. After formation of the complex for 2 hours, 25 µl of the treatment complex was injected into each tumor. The therapeutic oligonucleotide sequence is 5'-TGGTCTCCA-GGCTAGCTACAACGA-CCTGCACCT-3' (SEQ ID NO: 18) whereas the control antisense oligonucleotide sequence is 5'-TGCTCTCCA-GGCTATGTAGAACGA-CCTGCACCT-3' (SEQ ID NO:19). The only difference between the therapeutic DNAzyme sequence and the antisense sequences is that the nucleotides responsible for cleaving the mRNA have been altered with the antisense DNA. The tumor volume, measured before each injection, is given in the table below.

| Treatments | 1st Injection | 2nd Injection | 3rd Injection | 4th Injection | 5th Injection |
|---|---|---|---|---|---|
| Untreated | 9.2 (1.0) | 59.5 (9.5) | 163 (27) | 344.3 (64) | 570 (98) |
| HH-K4b | 9.5 (1.1) | 63.7 (10.7) | 134 (30) | 236 (55) | 429 (94) |
| HH-K4b + DNAzyme | 9.3 (1.3) | 35.0 (3.8) | 67 (15)* | 105.7 (25)* | 179 (54)* |
| HH-K4b + antisense | 12.4 (0.9) | 42.9 (8.1) | 133 (28) | 218 (54) | 334 (84) |

*$p < 0.05$, Untreated vs. HH-K4b-DNAzyme. The SEM of each treatment group is within the parentheses.
This demonstrates that branched histidine copolymer can deliver agents in vivo without a liposome component.

7. REFERENCES

Throughout this specification various patent and non-patent references have been mentioned. The entire disclosure of each such reference is incorporated herein by reference, as is the entire disclosure of each of the following references, to the extent relevant to making and using the invention as claimed:

1. Felgner, P. L. et al. 1987. Lipofection: a highly efficient, lipid-mediated DNA transfection procedure. *Proc. Natl. Acad. Sci. USA* 84:7413–7117.

2. Behr, J. P. et al. 1989. Efficient gene transfer into mammalian primary endocrine cells with lipopolyamine-coated DNA. *Proc. Natl. Acad. Sci. USA* 86:6982–6.

3. Remy, J. S., Sirlin, C., Vierling, P. and Behr, J-P. 1994. Gene transfer with a series of lipophilic DNA-binding molecules: *Bioconjugate Chem.* 5:647–654.

4. Nabel, G. L. et al. 1993. Direct gene transfer with DNA liposome complexes in melanoma expression, biological activity, and lack of toxicity in humans. *Proc. Natl. Acad. Sci. USA* 90:11307–311.

5. Zhu, N., Ligitt, D., Liu, Y., and Debs, R. 1993. Systemic gene expression after intravenous DNA delivery into adult mice. *Science* 261:209–211.

6. Thierry, A. R. et al. 1995. Systemic gene therapy: biodistribution and long-term expression of a transgene in mice. *Proc. Natl. Acad. Sci. USA* 92:9742–9746.

7. Marshall, J. 1995. The trouble with vectors. *Science* 269:1051–1055.

8. Xu, M. et al. 1996. Parenteral Gene Therapy with p53 inhibits human breast tumors in vivo through a bystander mechanism without evidence of toxicity. *Human Gene Ther.* 8:177–185.

9. Yang, J. P. and Huang, L. 1997. Overcoming the inhibitory effect of serum on lipofection by increasing the charge ratio of cationic liposome to DNA. *Gene Ther.* 4:950–960.

10. Liu, F., Qi, H., Huang, L, and Liu, D. 1997. Factor controlling the efficiency of cationic lipid-mediated transfection in vivo via intravenous administration. *Gene Ther.* 4:517–523.

11. Stewart, M. J. et al. 1992. Gene transfer in vivo with DNA-liposome complexes: safety and acute toxicity in mice. *Human Gene Ther.* 3:267–275.

12. Felgner, J. H. et al. 1994. Enhanced gene delivery and mechanism studies with a novel series of cationic lipid formulations. *J. Biol. Chem.* 269:2550–2561.

13. Liu, Y. et al. 1997. Factors influencing the efficiency of cationic liposome-mediated intravenous gene delivery. *Nature Biotechnology* 15:167–173.

14. Li, S., Rizzo, M. A., Bhattacharya, S., and Huang, L. 1988. Characterization of cationic lipid-protamine- DNA (LPD) complexes for intravenous gene delivery. *Gene Ther.* 5:930–937.

15. Gao, X and Huang, L. 1996. Potentiation of cationic liposome-mediated gene delivery by polycations. *Biochemistry* 35:1027–1036.

16. Sorgi, F. L., Bhattacharya, S., and Huang, L. 1997. Protamine sulfate enhances lipid-mediated gene transfer. *Gene Ther.* 4:961–968.

17. Li S., and Huang L. 1997. In vivo gene transfer via intravenous administration of cationic lipid-protamine-DNA (LPD) complexes. *Gene Ther.* 4:891–900.
18. Toncheva, V. et al. 1988. Novel vectors for gene delivery formed by self-assembly of DNA with poly (L-lysine) grafted with hydrophilic polymers. *Biochem. Biophys. Acta.* 1380:354–368.
19. Legendre, J. Y., and Szoka, Jr. F. C. 1992. Delivery of plasmid DNA into mammalian cell lines using pH-sensitive liposomes: comparison with cationic liposomes. *Pharm. Res.* 9:1235–1242.
20. Ogris, M. et al. 1998. The size of DNA/transferrin-PEI complexes is an important factor for gene expression in cultured cells. *Gene Ther.* 5:1425–1433.
21. Wolfert, M. A. and Seymour, L. W. 1998. Chloroquine and amphipathic peptide helices show synergistic transfection in vitro. *Gene Ther.* 5:409–414.
22. Erbacher, P. et al. 1996. Putative role of chloroquine in gene transfer into a human hepatoma cell line by DNA/lactosylated polylysine complexes. *Exp. Cell Res.* 225: 186–194.
23. Zauner W., Kichler A., Schmidt W., Merchtler K., and Wagner E. 1997. Glycerol and polylysine synergize in their ability to capture vesicular membranes: a mechanism for increased transferrin-polylysine-mediated gene transfer. *Exp. Cell Res.* 232:137–145.
24. Budker, V., Gurevich, V., Hagstrom, J. E., Bortzov, F., and Wolff, J. A. 1996. pH-sensitive cationic liposomes: a new synthetic virus-like vector. *Nature Biotechnology* 14:760–764.
25. Niidome T. et al. 1997. Binding of cationic a-helical peptides to plasmid DNA and their gene transfer abilities into cells. *J. Biol. Chem.* 272:15307–5312.
26. Boussif, O. et al. 1995. A versatile vector for gene and oligonucleotide transfer into cells in culture and in vivo: polyethylenimine. *Proc. Natl. Acad. Sci. USA* 92:7297–7301.
27. Behr, J. P. et al. 1989. Efficient gene transfer into mammalian primary endocrine cells with lipopolyamine-coated DNA. *Proc. Natl. Acad. Sci. USA* 86:6982–6986.
28. Remy, J. S. and Behr, J. P. 1996. Gene transfer with multivalent synthetic vectors. *J. Liposome Res.* 6:535–544.
29. Haensler J., and Szoka, Jr., F. C. 1993. Polyamidoamine cascade polymers mediate efficient transfection of cells in culture. *Bioconjugate Chem.* 4:372–379.
30. Midoux, P. and Monsigny, M. 1999. Efficient gene transfer by histidylated polylysine/pDNA complexes. *Bioconjugate Chem.* 10, 406–411.
31. Chen, Q. R., Kumar, D., Stass, S. A. and Mixson A. J. 1999. Liposomes complexed to plasmids encoding angiostatin and endostatin inhibit breast cancer in nude mice. *Cancer Res.* 59:3308–3312.
32. Cayot, P. and Tainturier, G. 1997. The quantification of protein amino groups by the trinitrobenzenesulfonic acid method: a reexamination. *Anal. Biochem.* 249:184–200.
33. Snyder, S. L. and Sobocinski, P. 1975. An improved 2,4,6-trinitrobenzenesulfonic acid method for the determination of amines. *Anal. Biochem.* 64:284–288.
34. Arap, W. et al. 1998. Cancer treatment by targeted drug delivery to tumor vasculature in a mouse model. *Science* 279:377–380.
35. Pasqualini, R. et al. 1997. Alpha v integrins as receptors for tumor targeting by circulating ligands. *Nat. Biotechnol.* 15:542–546.
36. Santoro, S. W., and Joyce, G. F. 1997. A general purpose RNA-cleaving DNA enzyme. *Proc. Natl. Acad. Sci. USA* 94, 4262–4266.
37. Marshall, J. et al. 1994. Stoichiometry of recombinant cystic fibrosis transmembrane conductance regulator in epithelial cells and its functional reconstitution into cells in vitro. *J. Biol Chem.* 269:2987–95.
38. Ramani, K, Bora, R. S., Kumar, M., Tyagi, S. K., and Sarkar, D. P. 1997. Novel gene delivery to liver cells using engineered virosomes. *FEBS Lett.* 404: 164–8.
39. Schoen, P., Chonn, A., Cullis, P. R. Wilschut J., and Scherrer, P. 1999. Gene transfer mediated by fusion protein hemagglutinin reconstituted in cationic lipid vesicles. *Gene Ther.* 6: 823–32.
40. Waelti, E. R. and Gluck, R. 1998. Delivery to cancer cells of antisense L-myc oligonucleotides incorporated in fusogenic, cationic-lipid-reconstituted influenza-virus envelopes (cationic virosomes). *Int J Cancer.* 77: 728–33.
41. Wu, P. et al. 1996. An AAV promoter-driven neuropeptide Y gene delivery system using Sendai virosomes for neurons and rat brain. *Gene Ther.* 3: 246–53.
42. Wagner, E. et al. 1992. Influenza virus hemagglutinin HA-2 N-terminal fusogenic peptides augment gene transfer by transferrin-polylysine-DNA complexes: toward a synthetic virus-like gene-transfer vehicle. *Proc. Natl. Acad Sci. USA.* 89: 7934–7938.
43. Curiel, D. T. et al. 1992. High-efficiency gene transfer mediated by adenovirus coupled to DNA-polylysine complexes. *Hum. Gene Ther.* 3: 147–54.
44. Curiel, D. T. 1994. High-efficiency gene transfer mediated by adenovirus-polylysine-DNA complexes. *Ann N Y Acad Sci.* 716: 36–56; discussion 56–58.

What is claimed is:

1. A pharmaceutical agent delivery composition comprising:
   (a) a transport polymer comprising a peptide, characterized as having at least 10 amino acid residues, and wherein at least 10% of said amino acid residues are histidine, and wherein at least 10% of said amino acid residues are selected from the group consisting of non-histidine amino acids with a side-group that carries a positive charge at physiological pH, and wherein the molecular structure of said peptide is selected from the group consisting of:
      linear, with the proviso that said peptide does not comprise a hexa-peptide having the sequence His-His-His-His-His-His, unless at least 10% of the remaining amino acid residues of said peptide are histidine; and
      branched, with a backbone peptide of 1 or more amino acid residues and at least one peptide branch of 1 or more amino acid residues covalently attached to a side-group of an amino acid residue of said backbone peptide, with the proviso that each peptide branch can consist of a single histidine residue only if the backbone peptide does not consist solely of lysine residues;
   with the proviso that said transport polymer does not consist of:
      a random histidine copolymer; or
      a block copolymer of histidine and a non-histidine amino acid with a side-group that carries a positive charge at physiological pH;
   (b) a pharmaceutical agent associated with said transport polymer; and
   (c) optionally, at least one intracellular delivery component associated with said transport polymer and/or said pharmaceutical agent.

2. The pharmaceutical agent delivery composition of claim 1, wherein at least 20% of the amino acid residues of said peptide are histidine, and wherein at least 20% of said amino acid residues are selected from the group consisting of non-histidine amino acids with a side-group that carries a positive charge at physiological pH.

3. The pharmaceutical agent delivery composition of claim 2, wherein about 40% to about 60% of the amino acid residues of said peptide are histidine.

4. The pharmaceutical agent delivery composition of claim 2, wherein said peptide comprises a subsegment of amino acid residues selected from the group consisting of:
   K-H-K-H-K-H-K-H-K-H (SEQ ID NO: 14),
   K-H-K-H-K-H-K-G-K-H-K-H-K (SEQ ID NO:1),
   K-H-K-H-K-H-K-G-K-H-K-H-K-H-K (SEQ ID NO:2),
   K-H-K-H-K-H-K-H-K-G-K-H-K-H-K-H-K-H-K (SEQ ID NO:3),
   K-H-K-H-K-H-K-H-K-G-K-H-K-H-K-H-K-H-K-G-K-H-K-H-K-H-K-H-K (SEQ ID NO:4),
   K-H-K-H-H-K-H-H-K-H-H-K-H-H-K-H-H-K-H-K (SEQ ID NO:5),
   K-K-H-H-H-K-H-H-H-K-K-H-H-H-K-H-H-H-K-K (SEQ ID NO:6),
   H-H-K-H-H-K-H-H-K-H-H-K-H-H-K (SEQ ID NO:15),
   K-K-H-K-H-K-H-K-G-K-H-K-H-K-H-K-H-K-K (SEQ ID NO:16),
   end-to-end repeats of one or more of the above sequences, and
   the reverse of any of the above sequences.

5. The pharmaceutical agent delivery composition of claim 2, further comprising at least one intracellular delivery component associated with said transport polymer and/or said pharmaceutical agent.

6. The pharmaceutical agent delivery composition of claim 5, wherein said intracellular delivery component comprises a lipid.

7. The pharmaceutical agent delivery composition of claim 2, further comprising a transition metal.

8. The pharmaceutical agent delivery composition of claim 2, wherein said pharmaceutical agent consists of at least one therapeutic agent.

9. The pharmaceutical agent delivery composition of claim 8, wherein said therapeutic agent is selected from the group consisting of a protein, an oligopeptide, a nucleic acid, a cancer chemotherapeutic agent, an infectious disease chemotherapeutic agent, and any combination of two or more of the above.

10. The pharmaceutical agent delivery composition of claim 9, wherein said therapeutic agent is nucleic acid.

11. The pharmaceutical agent delivery composition of claim 10, wherein said nucleic acid is an antisense oligonucleotide, a ribozyme, an RNA-cleaving DNA oligonucleotide, or a combination of two or more of the above.

12. The pharmaceutical agent delivery composition of claim 10, wherein at least about 40% of the amino acid residues of said peptide are histidine.

13. The pharmaceutical agent delivery composition of claim 12, wherein said pharmaceutical agent delivery composition further comprises an intracellular delivery component.

14. The pharmaceutical agent delivery composition of claim 13, wherein about 40% to about 60% of the amino acid residues of said peptide are histidine.

15. A method for delivering a pharmaceutical agent to the interior of a cell, said method comprising a step of contacting the cell with the pharmaceutical agent delivery composition of claim 1.

16. The method of claim 15, wherein at least 20% of the amino acids of said peptide are histidine and at least 20% of the non-histidine amino acid residues of said peptide carry a positive charge at physiological pH.

17. The method of claim 16, wherein the molecular structure of said peptide is branched.

18. The method of claim 16, wherein said peptide comprises a subsegment of amino acid residues selected from the group consisting of:
   K-H-K-H-K-H-K-H-K-H (SEQ ID NO: 14),
   K-H-K-H-K-H-K-G-K-H-K-H-K (SEQ ID NO:1),
   K-H-K-H-K-H-K-G-K-H-K-H-K-H-K (SEQ ID NO:2),
   K-H-K-H-K-H-K-H-K-G-K-H-K-H-K-H-K-H-K (SEQ ID NO:3),
   K-H-K-H-K-H-K-H-K-G-K-H-K-H-K-H-K-H-K-G-K-H-K-H-K-H-K-H-K (SEQ ID NO:4),
   K-H-K-H-K-H-H-K-H-H-K-H-H-K-H-H-K-H-K (SEQ ID NO:5),
   K-K-H-H-H-K-H-H-H-K-K-H-H-H-K-H-H-H-K-K (SEQ ID NO:6),
   H-H-K-H-H-K-H-H-K-H-H-K-H-H-K (SEQ ID NO:15),
   K-K-H-K-H-K-H-K-G-K-H-K-H-K-H-K-H-K-K (SEQ ID NO:16),
   end-to-end repeats of one or more of the above sequences, and
   the reverse of any of the above sequences.

19. The method of claim 16, wherein said pharmaceutical agent delivery composition further comprises at least one intracellular delivery component associated with said transport polymer and/or said pharmaceutical agent.

20. The method of claim 19, wherein said intracellular delivery component comprises a lipid.

21. The method of claim 16, wherein said pharmaceutical agent delivery composition further comprises a transition metal.

22. The method of claim 16, wherein about 40% to about 60% of the amino acids of said peptide are histidine.

23. The method of claim 16, wherein said pharmaceutical agent consists of at least one therapeutic agent.

24. The method of claim 23, wherein said therapeutic agent is selected from the group consisting of a protein, an oligopeptide, a nucleic acid, a cancer chemotherapeutic agent, an infectious disease chemotherapeutic agent, and any combination of two or more of the above.

25. The method of claim 24, wherein said therapeutic agent is nucleic acid.

26. The method of claim 25, wherein said nucleic acid is an antisense oligonucleotide, a ribozyme, an RNA-cleaving DNA oligonucleotide, or a combination of two or more of the above.

27. The method of claim 16, further comprising the steps of:
removing said cell from a subject prior to contacting said cell with said pharmaceutical agent delivery composition; and
administering said cell to said subject after contacting said cell with said pharmaceutical agent delivery composition.

28. The method of claim 27, wherein said pharmaceutical agent delivery composition further comprises an intracellular delivery component.

29. A method for producing a pharmaceutical agent delivery composition comprising the steps of:
a. providing a transport polymer comprising a peptide characterized as having at least 10 amino acid residues, and wherein at least 10% of said amino acid residues are histidine, and wherein at least 10% of said amino acid residues are selected from the group consisting of non-histidine amino acids with a side-group that carries a positive charge at physiological pH, and wherein the molecular structure of said peptide is selected from the group consisting of:
linear, with the proviso that said peptide does not comprise a sequence His-His-His-His-His-His, unless at least 10% of the remaining amino acid residues of said peptide are histidine; and branched, with a backbone peptide of 1 or more amino acid residues and at least one peptide branch of 1 or more amino acid residues covalently attached to a side-group of an amino acid residue of said backbone peptide, with the proviso that each peptide branch can consist of a single histidine residue only if the backbone peptide does not consist solely of lysine residues;
with the proviso that said transport polymer does not consist of:
a random histidine copolymer; or
a block copolymer of histidine and a non-histidine amino acid with a side-group that carries a positive charge at physiological pH;
b. providing a pharmaceutical agent capable of associating with said transport polymer;
c. combining said transport polymer with said pharmaceutical agent to form a polymer/pharmaceutical agent complex; and
d. mixing said complex with an intracellular delivery component.

30. The method of claim 29, wherein said intracellular delivery component comprises a lipid.

31. A pharmaceutical agent delivery composition comprising:
(a) a pharmaceutical agent;
(b) a transport polymer in association with the pharmaceutical agent, the transport polymer comprising a peptide characterized as having at least 10% of the amino acid residues are histidine and at least 10% of the amino acid residues are non-histidine, wherein the non-histidine residues are selected so as to tailor the transport polymer to the pharmaceutical agent and a method of association between the pharmaceutical agent and the transport polymer, and wherein the molecular structure of the peptide is selected from the group consisting of:
linear and having at least 13 amino acids, with the proviso that:
a. the entire sequence of said peptide cannot be described by the formula: $(XHHX)_n$, wherein H is histidine, X is a hydrophobic amino acid, and n is an integer greater than or equal to 4;
b. the entire sequence of said peptide cannot be described by the formula: $(XHXH)_n$, wherein H is histidine, X is a hydrophobic amino acid, and n is an integer greater than or equal to 4; and
c. said peptide does not comprise a hexa-peptide having the sequence His-His-His-His-His-His, unless at least 10% of the remaining amino acid residues of said peptide are histidine; and
branched and having at least 40 amino acids, with a backbone of 1 or more amino acid residues and at least one branch of 1 or more amino acid residues covalently attached to a side-group of an amino acid residue of said backbone, with the proviso that each branch can consist of a single histidine residue only if the backbone does not consist solely of lysine residues;
with the proviso that said transport polymer does not consist of:
a random histidine copolymer; or
a block copolymer of histidine and a non-histidine amino acid with a side-group that carries a positive charge at physiological pH; and
(c) optionally, at least one intracellular delivery component associated with said transport polymer and/or said pharmaceutical agent.

32. The pharmaceutical agent delivery composition of claim 31, further comprising a transition metal.

33. The pharmaceutical agent delivery composition of claim 31, wherein the pharmaceutical agent has an overall net negative charge, wherein at least 20% of the amino acid residues of said peptide are histidine, and wherein at least 20% of said amino acid residues are selected from the group consisting of non-histidine amino acids with a side-group that carries a positive charge at physiological pH.

34. The pharmaceutical agent delivery composition of claim 33, wherein about 40% to about 60% of the amino acids of said peptide are histidine.

35. The pharmaceutical agent delivery composition of claim 33, wherein the pharmaceutical agent comprises nucleic acid and wherein about 40% to about 60% of said amino acid residues of said peptide are histidine.

36. The pharmaceutical agent delivery composition of claim 35, wherein the non-histidine residues are each independently selected from the group consisting of lysine and glycine.

37. The pharmaceutical agent delivery composition of claim 35, wherein the molecular structure of the peptide is branched.

38. The pharmaceutical agent delivery composition of claim 35, wherein said peptide is selected from the group consisting of linear and having less than about 50 amino acids, and branched and having less than about 300 amino acids.

39. The pharmaceutical agent delivery composition of claim 35, further comprising at least one intracellular delivery component.

40. The pharmaceutical agent delivery composition of claim 39, wherein the intracellular delivery component comprises a lipid.

41. The pharmaceutical agent delivery composition of claim 40, wherein the lipid is a cationic lipid.

42. The pharmaceutical agent delivery composition of claim 40, wherein the molecular structure of the peptide is linear.

43. The pharmaceutical agent delivery composition of claim 33, wherein the pharmaceutical agent comprises a therapeutic agent selected from the group consisting of an antisense oligonucleotide, a ribozyme, an RNA-cleaving DNA oligonucleotide, an expression vector, and a combination of two or more of the above.

44. The pharmaceutical agent delivery composition of claim 43, wherein the therapeutic agent is an RNA-cleaving DNA oligonucleotide which targets VEGF receptor mRNA.

45. The pharmaceutical agent delivery composition of claim 33, wherein said peptide comprises a segment of amino acid residues selected from the group consisting of:
K-H-K-H-K-H-K-H-K-H (SEQ ID NO: 14),
K-H-K-H-K-H-K-G-K-H-K-H-K (SEQ ID NO:1),
K-H-K-H-K-H-K-G-K-H-K-H-K-H-K (SEQ ID NO:2),
K-H-K-H-K-H-K-H-K-G-K-H-K-H-K-H-K (SEQ ID NO:3),
K-H-K-H-K-H-K-H-K-G-K-H-K-H-K-H-K-H-K-G-K-H-K-H-K-H-K (SEQ ID NO:4),
K-H-K-H-H-K-H-H-K-H-H-K-H-H-K-H-H-K-H-K (SEQ ID NO:5),
K-K-H-H-H-K-H-H-H-K-K-H-H-H-K-H-H-H-K-K (SEQ ID NO:6),
H-H-K-H-H-K-H-H-K-H-H-K-H-H-K (SEQ ID NO:15),
K-K-H-K-H-K-H-K-H-K-G-K-H-K-H-K-H-K-K (SEQ ID NO:16),
end-to-end repeats of one or more of the above sequences, and the reverse of any of the above sequences.

46. A method for delivering a pharmaceutical agent to the interior of a cell, said method comprising a step of contacting the cell with the pharmaceutical agent delivery composition of claim 31.

47. The method of claim 46, wherein the pharmaceutical agent has an overall net negative charge, wherein at least 20% of the amino acid residues of said peptide are histidine, and wherein at least 20% of said amino acid residues are selected from the group consisting of non-histidine amino acids with a side-group that carries a positive charge at physiological pH.

48. The method of claim 47, wherein the pharmaceutical agent comprises nucleic acid and wherein about 40% to about 60% of said amino acid residues of said peptide are histidine.

49. The method of claim 48, wherein the non-histidine residues are each independently selected from the group consisting of lysine and glycine.

50. The method of claim 47, wherein the pharmaceutical agent delivery composition further comprises at least one intracellular delivery component, wherein the intracellular delivery component comprises a cationic lipid.

51. The method of claim 47, wherein about 40% to about 60% of the amino acids of said peptide are histidine.

* * * * *

SEQUENCE LISTING

<160> NUMBER OF SEQ ID NOS: 16

<210> SEQ ID NO 1
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 1

Lys His Lys His Lys His Lys Gly Lys His Lys His Lys
1               5                   10

```
<210> SEQ ID NO 2
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 2

Lys His Lys His Lys His Lys Gly Lys His Lys His Lys His Lys
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 3

Lys His Lys His Lys His Lys His Lys Gly Lys His Lys His Lys His
1               5                   10                  15

Lys His Lys

<210> SEQ ID NO 4
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 4

Lys His Lys His Lys His Lys His Lys Gly Lys His Lys His Lys His
1               5                   10                  15

Lys His Lys Gly Lys His Lys His Lys His Lys His Lys
                20                  25

<210> SEQ ID NO 5
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 5

Lys His Lys His His Lys His His Lys His His Lys His His Lys His
1               5                   10                  15

His Lys His Lys
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 6

Lys Lys His His His Lys His His His Lys Lys His His His Lys His
1               5                   10                  15

His His Lys Lys
            20

<210> SEQ ID NO 7
<211> LENGTH: 29
```

```
<212> TYPE: PRT
<213> ORGANISM: Artificial Sequence
<220> FEATURE:
<223> OTHER INFORMATION: Synthetic Peptide

<400> SEQUENCE: 7

Tyr Gly Arg Lys Lys Arg Arg Gln Arg Arg Gly Lys His Lys His
1               5                   10                  15

Lys His Lys His Lys His Lys His Lys His Lys
            20                  25

<210> SEQ ID NO 8
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 8

Tyr Gly Arg Lys Lys Arg Arg Gln Arg Arg His His Lys His His
1               5                   10                  15

Lys His His Lys His His Lys His His Lys
            20                  25

<210> SEQ ID NO 9
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 9

Lys Lys His Lys His Lys His Lys His Lys Gly Lys His Lys His Lys
1               5                   10                  15

His Lys His Lys Lys
            20

<210> SEQ ID NO 10
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 10

Lys Ser Lys Ser Lys Ser Lys Ser Lys Gly Lys Ser Lys Ser Lys Ser
1               5                   10                  15

Lys Ser Lys

<210> SEQ ID NO 11
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 11

Ser His Ser His Ser His Ser His Ser Gly Ser His Ser His Ser His
1               5                   10                  15

Ser His Ser

<210> SEQ ID NO 12
<211> LENGTH: 19
<212> TYPE: PRT
```

```
<213> ORGANISM: Artificial Sequence
<220> FEATURE:
<223> OTHER INFORMATION: Synthetic Peptide

<400> SEQUENCE: 12

Lys Lys Lys Lys Lys Lys Lys Lys Gly Lys Lys Lys Lys Lys
1               5                   10                  15

Lys Lys Lys

<210> SEQ ID NO 13
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 13

Arg His Arg His Arg His Arg His Arg Gly Arg His Arg His Arg His
1               5                   10                  15

Arg His Arg

<210> SEQ ID NO 14
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 14

Lys His Lys His Lys His Lys His Lys His
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

His His Lys His His Lys His His Lys His His Lys His His Lys
1               5                   10                  15

<210> SEQ ID NO 16
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 16

Lys Lys His Lys His Lys His Lys His Lys Gly Lys His Lys His Lys
1               5                   10                  15

His Lys His Lys Lys
            20
```